(12) United States Patent
Rogers, Jr. et al.

(10) Patent No.: US 8,460,411 B2
(45) Date of Patent: Jun. 11, 2013

(54) MICROCHANNEL COMPRESSION REACTOR

(75) Inventors: William Allen Rogers, Jr., Marysville, OH (US); Christopher Paul Weil, Pickerington, OH (US); Robert Dwayne Litt, Westerville, OH (US); Ronald Chester Pasadyn, Missouri City, TX (US); George Bradley Smith, Rock Hill, SC (US); Charles Robert Miele, Columbus, OH (US); Thomas Peter Forte, Columbus, OH (US); Jimmy Glen Pelham, Bartlesville, OK (US)

(73) Assignee: Velocys, Inc., Plain City, OH (US)

( * ) Notice: Subject to any disclaimer, the term of this patent is extended or adjusted under 35 U.S.C. 154(b) by 0 days.

(21) Appl. No.: 12/819,427

(22) Filed: Jun. 21, 2010

(65) Prior Publication Data

US 2011/0004345 A1    Jan. 6, 2011

Related U.S. Application Data

(62) Division of application No. 10/774,298, filed on Feb. 6, 2004, now abandoned.

(51) Int. Cl.
    *C01B 6/24*    (2006.01)
    *C01B 3/36*    (2006.01)
    *B01J 3/00*    (2006.01)
    *B01J 8/00*    (2006.01)

(52) U.S. Cl.
    USPC ......... 48/197 R; 422/242; 422/625; 422/626; 422/629; 423/644

(58) Field of Classification Search
    USPC ................................. 48/197 R; 422/625–629
    See application file for complete search history.

(56) References Cited

U.S. PATENT DOCUMENTS

| | | | |
|---|---|---|---|
| 2,462,517 | A | 2/1949 | Leverenz |
| 2,997,435 | A | 8/1961 | Millar et al. |

(Continued)

FOREIGN PATENT DOCUMENTS

| | | |
|---|---|---|
| DE | 200 18 916 U 1 | 3/2002 |
| EP | 1 400 280 A1 | 3/2004 |

(Continued)

OTHER PUBLICATIONS

Freemantle, Michael, Microprocessing on a Large Scale, Chemical & Engineering News, Oct. 11, 2004, copyright 2004, pp. 39-43, vol. 82, No. 41, American Chemical Society, USA.

(Continued)

*Primary Examiner* — Matthew Merkling
(74) *Attorney, Agent, or Firm* — Taft Stettinius & Hollister LLP

(57) ABSTRACT

A process unit comprising: (a) a first microchannel module comprising: (i) a first unit operation including microchannels, in which at least a portion of a unit operation takes place, adapted to be in fluid communication with a first inlet stream and a first outlet stream, and (ii) a second unit operation including microchannels adapted to be in thermal communication with the first unit operation, the second unit operation adapted to be in fluid communication with a second inlet stream and a second outlet stream; and (b) a pressurized vessel at least partially containing the first microchannel module adapted to be concurrently occupied by a compressive medium in thermal communication with the first microchannel module.

16 Claims, 15 Drawing Sheets

U.S. PATENT DOCUMENTS

| | | | |
|---|---|---|---|
| 3,515,520 | A | 6/1970 | Hervert |
| 4,167,915 | A | 9/1979 | Toole et al. |
| 4,670,404 | A | 6/1987 | Swift et al. |
| 5,167,930 | A | 12/1992 | Fassbender |
| 5,340,663 | A * | 8/1994 | Buswell et al. ............... 429/423 |
| 5,811,062 | A * | 9/1998 | Wegeng et al. ............... 422/129 |
| 5,932,182 | A | 8/1999 | Blaney |
| 6,126,723 | A | 10/2000 | Drost et al. |
| 6,159,434 | A | 12/2000 | Gonjo et al. |
| 6,190,624 | B1 | 2/2001 | Romatier |
| 6,192,596 | B1 | 2/2001 | Bennett et al. |
| 6,200,536 | B1 | 3/2001 | Tonkovich et al. |
| 7,118,917 | B2 | 10/2006 | Bergh et al. |
| 7,172,735 | B1 | 2/2007 | Lowe et al. |
| 7,234,514 | B2 | 6/2007 | Vogel |
| 2002/0028164 | A1 | 3/2002 | Schutte et al. |
| 2002/0182735 | A1 | 12/2002 | Kibby et al. |
| 2004/0081600 | A1 | 4/2004 | Moreno et al. |
| 2005/0025677 | A1 | 2/2005 | Oberbeck et al. |

FOREIGN PATENT DOCUMENTS

| | | |
|---|---|---|
| EP | 05 71 3077 | 3/2013 |
| GB | 2 128 013 A | 4/1984 |
| WO | WO 01/41916 A1 | 6/2001 |
| WO | WO 2005/077516 A1 | 8/2005 |
| WO | PCT/US2005/003904 | 8/2006 |

OTHER PUBLICATIONS

Thayer, Ann M., Harnessing Microreactions, Chemical & Engineering News, May 30, 2005, copyright 2005, pp. 43-52, vol. 83., No. 22, American Chemical Society USA.

Wang, et al., Intensification of Gas-To-Liquid (GTL) Process Using Microchannel Technology, May 5, 2003, Pacific Northwest National Laboratory, Richland, WA and Velocys, Inc., Columbus, Ohio, USA.

Driscol, et al., 300 MWe Supercritical CO2 Plant Layout and Design, Topical Report, Report No. MIT-GFR-014, Jun. 2004, Center for Advanced Nuclear Energy Systems, MIT Nuclear Engineering Department, Cambridge, MA., USA.

Levent et al., "Production of hydrogen-rich gases from steam reforming of methane in an automatic catalytic microreactor", International Journal of Hydrogen Energy 28, (2003) pp. 945-959, © 2003, Published by Elsevier Science Ltd.

* cited by examiner

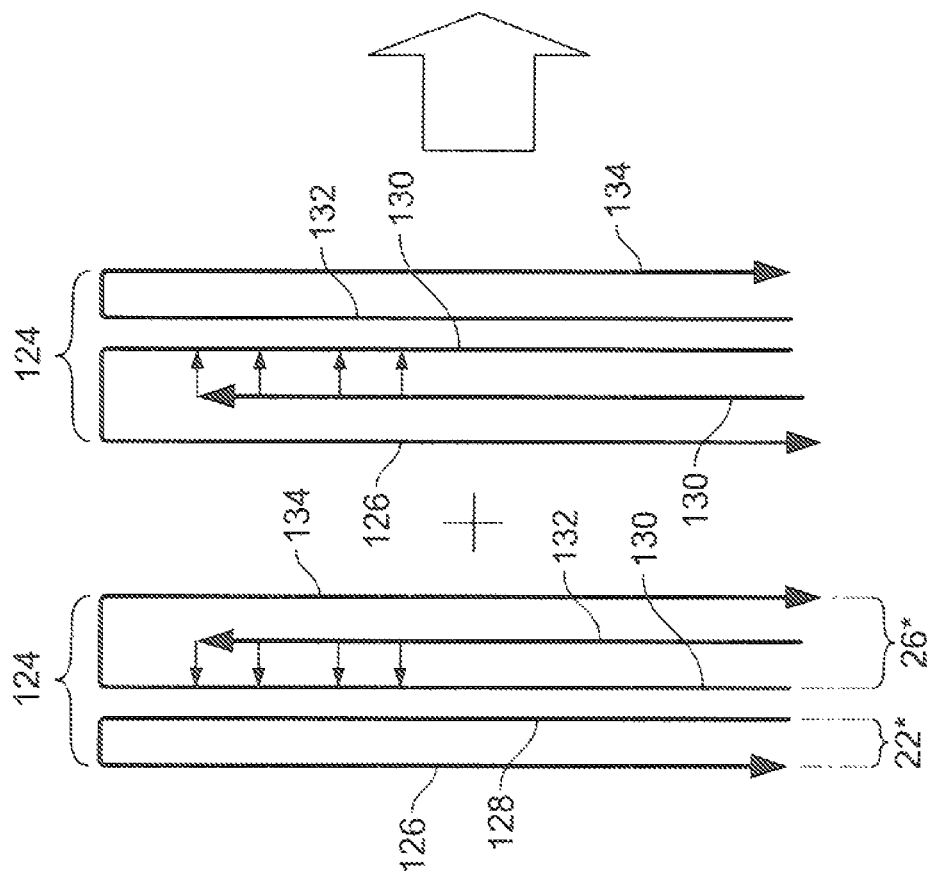
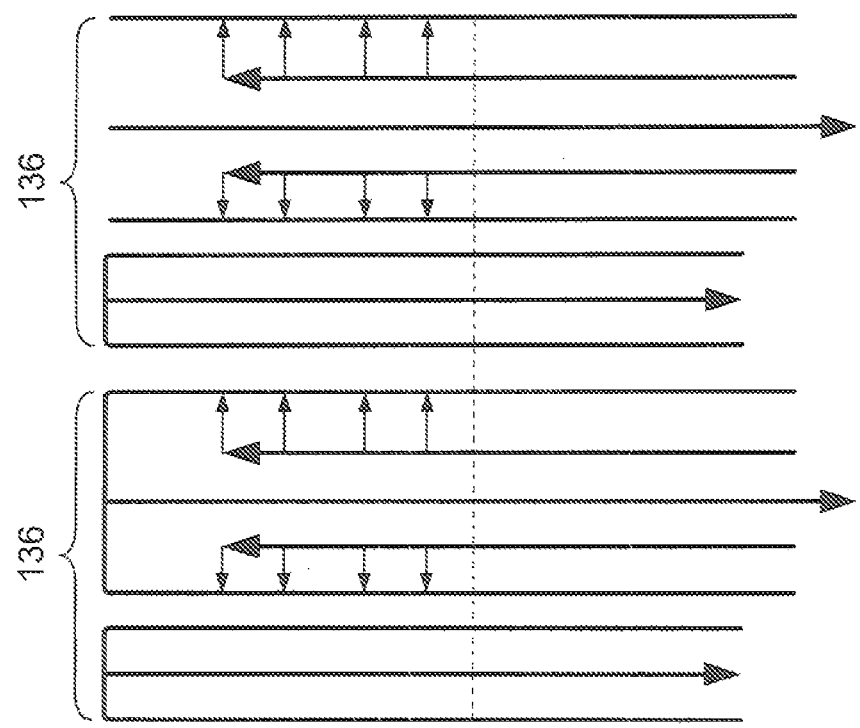
FIG. 10
FIG. 11

MICROCHANNEL COMPRESSION REACTOR

CROSS-REFERENCE TO RELATED APPLICATIONS

This application is a divisional of and claims priority to U.S. patent application Ser. No. 10/774,298, filed on Feb. 6, 2004 now abandoned, the disclosure of which is hereby incorporated by reference.

BACKGROUND

The present disclosure is related to unit operations where at least a portion of the unit operation is in compression; and more particularly, to unit operations where at least a portion of the unit operation is contained within a pressure vessel and maintained in compression.

Prior art disclosures, such as U.S. Pat. No. 5,167,930, disclose a sealed chamber encasing a reactor, where the pressure within the sealed chamber equals that of the reactor. The equalization of pressures between reactor and chamber is maintained by providing an expandable reactor and an expandable sealed chamber that accommodated for such changes.

Other prior art disclosures, such as U.S. Pat. No. 3,515,520, disclose a reactor with an internal corrosion resistant sleeve adapted to receive a catalyst and/or a corrosive reactant therein. The sleeve is jacketed by a higher-pressure flow of a non-corrosive reactant to prohibit leaks in the sleeve from leaking the corrosive reactant and/or catalyst and making contact with the exterior reactor walls. The non-corrosive reactant enters the sleeve through an opening and exits via another opening in fluid communication with the catalyst/corrosive reactant and is thereafter consumed through the normal reaction process.

Still further prior art disclosures, such as U.S. Pat. No. 2,462,517, disclose a multiple walled reactor where an internal, first wall confines the reaction chamber, and a second wall defines a cavity occupied by a pressurized atmosphere, and a third wall defines a cavity occupied by a cooling fluid. The pressurized atmosphere is used to regulate the external reactor vessel pressure, while the cooling fluid is used to regulate the thermal energy within the pressurized reservoir and the reactor.

SUMMARY

The present disclosure is related to unit operations where at least a portion of the unit operation is in compression; and more particularly, to unit operations where at least a portion of the unit operation is contained within a pressure vessel and maintained in compression by a compressive medium that may include, without limitation, an inert medium and a chemical reactant. The compressive nature of the medium ensures that a leak within the unit operation will result in the ingress of the medium into the unit operation and inhibit the egress of any material from the unit operation. A unit operation may include one or more of a chemical reactor, a mixer, a chemical separation unit, and a heat exchanger. A chemical separation unit may perform, without limitation, distillation, extraction, absorption, and adsorption. A further detailed embodiment makes available an inert medium generally isothermal with the unit operation to concurrently maintain compression of the unit operation and provide a sufficient source of the inert medium for purging a chemical reactor of the unit operation during a reactor shutdown procedure.

The present disclosure is also related to chemical reactors, which utilize microchannel technology, in which at least a portion of the reaction takes place within the microchannels. More specifically, the present disclosure makes use of a chemical reactor comprising a plurality of microchannels maintained in compression from a compressive, possibly inert, medium external thereto. Even more specifically, the inert medium may provide heating or cooling of the microchannels and, when applicable, a blocking medium to inhibit reactant and/or product from exiting the chemical reactor if the integrity of the reactor has been compromised and/or to purge the reactor during a shutdown procedure.

Accordingly, it is a first aspect of the invention to provide a chemical process system comprising: (a) a first unit operation adapted to be in fluid communication with an inlet stream and an outlet stream; (b) a pressure vessel at least partially containing the first unit operation therein, the pressure vessel concurrently adapted to be occupied by an inert medium to compress the first unit operation; and (c) a purge stream adapted to be in fluid communication with an inert medium source for selectively conveying the inert medium from the inert medium source and into fluid communication with the first unit operation.

In a detailed embodiment of the first aspect, the first unit operation includes a chemical reactor. In a more detailed embodiment, the chemical process system includes a second unit operation in thermal communication with the first unit operation. In yet a further detailed embodiment, the second unit operation includes at least one of a heat exchanger and a chemical reactor. In another more detailed embodiment, at least one of the first unit operation and the second unit operation includes microchannels. In yet another more detailed embodiment, the chemical reactor includes microchannels, the inlet stream includes a first reactant stream, and the outlet stream includes a first product stream. In a further detailed embodiment, the first unit operation is at least one of cooled and heated at least in part by the inert medium. In still a further more detailed embodiment, the inert medium includes at least one of helium, neon, argon, krypton, xenon, water and nitrogen. In yet a further more detailed embodiment, the microchannels include a catalyst. In another detailed embodiment, the catalyst comprises at least one of a catalytic lining, a catalytic pellet, and a catalytic insert. In yet another more detailed embodiment, the inert medium within the pressure vessel is in fluid communication with at least one of a heat exchanger, a compressor, and an inert medium source. In still a further more detailed embodiment, the chemical process system includes a controller operatively coupled to a first sensor monitoring an internal pressure within the pressure vessel and a second sensor monitoring an internal pressure within the first unit operation, where the controller is responsive to data generated by the first sensor and the second sensor to operate the pressure vessel at a higher pressure than the first unit operation.

In an alternate detailed embodiment of the first aspect, the controller is operatively coupled to a vent valve in fluid communication with the pressure vessel to selectively vent at least a portion of the inert medium within the pressure vessel to decrease the internal pressure within the pressure vessel. In a further detailed embodiment, the controller is operative to detect a leak within the first unit operation from the data generated by the first sensor. In yet a further detailed embodiment, the second unit operation is at least partially contained within the pressure vessel.

It is a second aspect of the invention to provide a chemical process system comprising: (a) a first unit operation including microchannels adapted to be in fluid communication with an inlet stream and an outlet stream; (b) a second unit operation in thermal communication with the first unit operation; and (c) a pressure vessel at least partially containing the first unit operation therein and concurrently occupied by a compressive medium adapted to maintain the first unit operation in compression.

In a detailed embodiment of the second aspect, the second unit operation includes at least one of a heat exchanger and a chemical reactor. In a more detailed embodiment, the second unit operation includes a chemical reactor adapted to be in fluid communication with a reactant stream and a product stream. In yet a further detailed embodiment, the second unit operation also includes a heat exchanger facilitating thermal energy transfer between the second unit operation and the first unit operation. In yet another more detailed embodiment, the second unit operation includes a heat exchanger facilitating thermal energy transfer between the second unit operation and the first unit operation. In a further detailed embodiment, the chemical process system includes a purge stream in fluid communication with the compressive medium and in selective fluid communication with the first unit operation. In still a further more detailed embodiment, the first unit operation and the second unit operation each include at least one of a chemical reactor, a heat exchanger, a mixer, and a separation unit.

In a further detailed embodiment of the second aspect, the pressure vessel at least partially contains the second unit operation. In a more detailed embodiment, the second unit operation includes microchannels, and the first unit operation and the second unit operation are coupled together in a single microchannel module. In yet a further detailed embodiment, the first unit operation and/or the second unit operation includes a chemical reactor, the first and/or second unit operation includes a catalyst in series with the microchannels thereof, and the catalyst comprises at least one of a catalytic lining, a catalytic pellet, and a catalytic insert. In yet another more detailed embodiment, the pressure vessel at least partially contains a plurality of microchannel modules therein. In a further detailed embodiment, at least one of the microchannels of the first unit operation and the microchannels of the second unit operation include a catalyst in series therewith, and the microchannels at least one of upstream and downstream from the catalyst comprise a heat exchanger. In still a further more detailed embodiment, the microchannels of the first unit operation are adapted to carry a first fluid in a first direction and the microchannels of the second unit operation are adapted to carry a second fluid in a second direction, where the first direction and the second direction may be different. In yet another more detailed embodiment, the chemical process system includes a controller to regulate an internal pressure within the pressure vessel, and where the pressure vessel includes a recycle stream for cycling the compressive medium into and out of the pressure vessel It is a third aspect of the present invention to provide a method of starting up one or more unit operations, the method comprising the steps of: (a) feeding a material to a first unit operation including microchannels therein; (b) processing, within the first unit operation, at least a portion of the material; (c) monitoring at least one of internal pressure, temperature, and concentration within the first unit operation or downstream from the first unit operation; and (d) pressurizing a containment device, at least partially containing the first unit operation therein, with a compressive medium to maintain a pressure differential between an internal pressure within the containment device and an internal pressure within the first unit operation such that the internal pressure within the containment device is greater than the internal pressure within the first unit operation.

In a detailed embodiment of the third aspect, the method includes the step of adjusting the internal pressure within the containment device to track the internal pressure within the first unit operation. In a more detailed embodiment, the first unit operation includes a tubular flow reactor. In yet a further detailed embodiment, the pressurizing step includes the step of monitoring the internal pressure within the containment device. In another more detailed embodiment, the pressurizing step includes providing selective fluid communication between the containment device and a compressive medium source. In yet another more detailed embodiment, the compressive medium includes at least one of an inert medium, the material fed to the unit operation, and the processed material exiting the unit operation. In a further detailed embodiment, the method includes the steps of feeding a composition to a second unit operation, processing, within the second unit operation, at least a portion of the composition, monitoring at least one of internal pressure, temperature, and concentration within the second unit operation or downstream from the second unit operation, and pressurizing the containment device, at least partially containing the second unit operation therein, with the compressive medium to maintain the pressure differential between the internal pressure within the containment device and an internal pressure within the second unit operation such that the internal pressure within the containment device is greater than the internal pressure within the second unit operation. In still a further more detailed embodiment, the second unit operation includes microchannels through which the composition may flow therethrough.

It is a fourth aspect of the present invention to provide a method of shutting down one or more unit operations, the method comprising the steps of: (a) containing at least a portion of a first unit operation, including microchannels, within a pressure containment vessel including an inert medium operative to compress the first unit operation; (b) decreasing material within a supply stream entering the first unit operation; (c) directing inert medium into fluid communication with the first unit operation to provide an inert concentration within the first unit operation; (d) monitoring at least one of pressure, temperature, and concentration at least one of within and downstream from the first unit operation; and (e) increasing the inert medium concentration within the first unit operation.

In a detailed embodiment of the fourth aspect, the containing step includes the step venting the inert medium to a lower pressure sink to reduce an internal pressure of the pressure containment vessel. In a more detailed embodiment, the directing step includes directing at least a portion of the inert medium from the pressure containment vessel into fluid communication with the first unit operation to provide the inert concentration within the first unit operation. In yet a further detailed embodiment, the method includes the steps of containing at least a portion of a second unit operation within the pressure containment vessel including the inert medium operative to compress the second unit operation, decreasing a feed supply within a feed supply stream entering the second unit operation, and monitoring at least one of pressure, temperature, and concentration at least one of within and downstream from the second unit operation. In another more detailed embodiment, the method includes the steps of directing inert medium into fluid communication with the second unit operation to provide an inert concentration within the second unit operation, and increasing the inert medium concentration within the second unit operation. In yet another more detailed embodiment, the second unit operation includes microchannels.

It is a fifth aspect of the present invention to provide a unit operation containment system comprising: (a) a first unit operation including microchannels adapted to be coupled to a supply stream and an outlet stream; (b) a pressure containment device adapted to maintain at least a portion of the first unit operation in compression via a pressurized medium, where the pressure containment device is in selective fluid communication with a medium source; and (c) a controller operatively coupled to at least a first system sensor detecting an internal pressure within the first unit operation and a second system sensor detecting an internal pressure within the pressure containment device, the controller being responsive to data generated by the first system sensor and the second system sensor to adjust the internal pressure within the pressure containment device.

In a detailed embodiment of the fifth aspect, the first unit operation includes a plurality of microchannels in which at least a portion of a chemical reaction takes place. In a more detailed embodiment, the unit operation containment system includes a second unit operation in thermal communication with the first unit operation. In yet a further detailed embodiment, the second unit operation includes microchannels therein, where the microchannels of the second unit operation are coupled to the microchannels of the first unit operation to provide an integrated module. In another more detailed embodiment, the pressure containment device includes an integrated module at least partially housed therein, the first unit operation includes a chemical reactor, the second unit operation includes at least one of a chemical reactor and a heat exchanger, the chemical reactor of the first unit operation is housed within the pressure containment device, and at least one of a chemical reactor and a heat exchanger of the second unit operation are housed within the pressure containment device. In yet another more detailed embodiment, the controller is operatively coupled to a control valve in fluid communication with the medium source and upstream from the pressure containment device to selectively provide the pressurized medium to the containment device and increase the internal pressure therein in response to data received from the first sensor and the second sensor, and the pressure containment device includes an outlet stream including a vent valve in series therewith to vent excess pressurized medium from the pressure containment device. In a further detailed embodiment, the pressure containment device includes a purge valve in series therewith, operatively coupled to the controller, and in selective fluid communication with the first unit operation. In still a further more detailed embodiment, the second unit operation includes a chemical reactor in thermal communication with the chemical reactor of the first unit operation.

In a detailed embodiment of the fifth aspect, the first unit operation includes a heat exchanger comprising microchannels at least one of upstream and downstream from the chemical reactor of the first unit operation, and the second unit operation includes a heat exchanger comprising microchannels at least one of upstream and downstream from the chemical reactor of the second unit operation and in thermal communication with the heat exchanger of the first unit operation. In yet another more detailed embodiment, the recycle stream is in series with a compressor, a pump, a condenser, and a heat exchanger. In still a further more detailed embodiment, a volume of the inert medium within the pressure containment device is available to purge the reactor. In a more detailed embodiment, the pressure containment vessel includes a recycle stream, and the recycle stream is in series with a compressor, a condenser, and a heat exchanger. In yet a further detailed embodiment, the second unit operation includes microchannels therein, the pressurized vessel includes at least one refurbishment line to refurbish a catalyst in series with a chemical reactor of the first unit operation. In another more detailed embodiment, the pressurized medium includes an inert medium, and the inert medium within the pressure containment device is in selective fluid communication with a chemical reactor of the first unit operation It is a sixth aspect of the present invention to provide a process unit comprising a first microchannel module comprising: (a) a first unit operation including microchannels, in which at least a portion of a unit operation takes place, adapted to be in fluid communication with a first inlet stream and a first outlet stream, a second unit operation including microchannels adapted to be in thermal communication with the first unit operation, the second unit operation adapted to be in fluid communication with a second inlet stream and a second outlet stream; and (b) a pressurized vessel, at least partially containing the first microchannel module, adapted to be concurrently occupied by a compressive medium in thermal communication with the first microchannel module.

In a detailed embodiment of the sixth aspect, at least one microchannel of the first unit operation is adjacent to at least one microchannel of the second unit operation and in thermal communication therewith, while at least one of a chemical reactor, a mixer, a chemical separation unit, and a heat exchanger includes at least one microchannel of the first unit operation, and at least one of a chemical reactor, a mixer, a chemical separation unit, and a heat exchanger includes at least one microchannel of the second unit operation. In a more detailed embodiment, the first unit operation includes a chemical reactor including at least one microchannel, while at least one microchannel of the first unit operation includes a catalyst in series therewith, and the catalyst comprises at least one of a catalytic lining, a catalytic pellet, and a catalytic insert. In yet a further detailed embodiment, the chemical reactor of the first unit operation houses the catalyst therein, while at least one microchannel of the first unit operation is adjacent to at least one microchannel of the second unit operation, and at least one microchannel of the first unit operation is adapted to carry a first fluid therein in a first direction and at least one microchannel of the second unit operation is adapted to carry a second fluid in a second direction. In another more detailed embodiment, the pressurized vessel is generally cylindrical in shape, and the first microchannel module is generally rectangular in cross-section. In yet another more detailed embodiment, at least one of the first unit operation and the second operation is in fluid communication with the open atmosphere. In a further detailed embodiment, the first unit operation includes a first chemical reactor adapted to receive a first reactant feed via the first inlet stream, the second unit operation includes a second chemical reactor adapted to receive a second reactant feed via the second inlet stream, the first chemical reactor and the second chemical reactor are adapted to be maintained in compression by the compressive medium within the pressurized vessel, and the first microchannel module comprises a plurality of laminated sheets.

It is a seventh aspect of the present invention to provide a process unit comprising: (a) a first chemical reactor including microchannels adapted to be in fluid communication with a first reactant stream and a first product stream; (b) a second chemical reactor including microchannels adapted to be in thermal communication with the first chemical reactor, where the microchannels of the second chemical reactor are adapted to be in fluid communication with a second reactant stream and a second product stream; and (c) a pressurized vessel containing the first chemical reactor and the second chemical reactor, where the pressurized vessel is adapted to be concurrently occupied by a compressive medium in thermal communication with the first chemical reactor.

In a detailed embodiment of the seventh aspect, the compressive medium includes water and the pressurized vessel is an elevated temperature water source. In a more detailed embodiment, the compressive medium includes an inert medium. In yet a further detailed embodiment, the first chemical reactor accommodates a throughput of between 100 liters per hour to approximately 10,000 liters per hour. In another more detailed embodiment, the process unit includes a vent valve in fluid communication with the pressurized vessel. In yet another more detailed embodiment, the process unit includes a controller operatively coupled to sensors associated with the pressurized vessel and the first chemical reactor, wherein the controller is operative to maintain an internal pressure within the pressurized chamber to be greater than an internal pressure within the first chemical reactor. In a further detailed embodiment, a purge stream providing selective fluid communication between an interior of the pressurized vessel and an interior of the first chemical reactor. In yet a further detailed embodiment, the process unit includes a recycle stream for cycling the inert medium into and out of the pressurized vessel, wherein a heat exchanger is in thermal communication with the recycle stream. In yet another more detailed embodiment, the process unit includes a first heat exchanger comprising microchannels in fluid communication with the microchannels of the first chemical reactor, a second heat exchanger comprising microchannels in fluid communication with the microchannels of the second chemical reactor, at least a portion of the microchannels of the first heat exchanger are housed within the pressurized vessel, and at least a portion of the microchannels of the second heat exchanger are housed within the pressurized vessel. In a further detailed embodiment, the first fluid includes a product from an exothermic or endothermic reaction, and the second fluid includes a reactant for an endothermic or an exothermic reaction.

It is an eighth aspect of the present invention to provide a process unit comprising: (a) a chemical process conduit including microchannels adapted to be in fluid communication with a chemical process stream; and (b) a pressurized vessel containing at least a portion of the chemical process conduit, where the pressurized vessel is adapted to be concurrently occupied a compressed medium and at least the portion of the chemical process conduit, where at least one of the chemical process conduit and the process conduit includes microchannels, and where at least a portion of the chemical process conduit is maintained in compression by the compressed medium within the pressurized vessel.

In a detailed embodiment of the eighth aspect, the process unit includes a process conduit in thermal communication with the chemical process conduit and in fluid communication with a process conduit stream. In a more detailed embodiment, a first reaction occurs within the microchannels of the chemical process conduit, and the chemical process stream is adapted to be in fluid communication with a reactant supply stream and a product stream. In yet a further detailed embodiment, the process conduit includes microchannels, while a second reaction occurs within the microchannels of the process conduit, and the process conduit stream is adapted to be in fluid communication with a second reactant supply stream and a second product stream. In another more detailed embodiment, the process unit includes a heat exchange recuperator adapted to exchange thermal energy with at least one of the reactant supply stream, the product stream, the second reactant supply stream, and the second product stream. In yet another more detailed embodiment, the heat exchange recuperator includes microchannels. In a further detailed embodiment, the heat exchange recuperator is at least partially contained within the pressurized vessel. In yet a further detailed embodiment, the microchannels of the chemical process stream are wholly contained within the pressurized vessel, while the microchannels of the process conduit are wholly contained within the pressurized vessel, and the microchannels of the heat exchange recuperator are wholly contained within the pressurized vessel. In yet another more detailed embodiment, the compressed medium contained within the pressurized vessel includes an inert medium. In a further detailed embodiment, the compressed medium contained within the pressurized vessel includes a reactant from at least one of the reactant supply stream and the second reactant supply stream. In still a further detailed embodiment, the compressed medium contained within the pressurized vessel includes a product from at least one of the product stream and the second product stream.

It is a ninth aspect of the present invention to provide a method of operating a unit operation comprising the steps of: (a) containing a first microchannel module at least partially within a pressurized vessel, the first microchannel module comprising a first unit operation and a second unit operation, where the first unit operation and the second unit operation each include at least one of a chemical reactor, a mixer, a chemical separation unit, and a heat exchanger; (b) pressurizing the first unit operation and the second unit operation with a compressive medium within the pressurized vessel; (c) operating the first unit operation and the second unit operation to include passing a first fluid through the first unit operation and a second fluid through the second unit operation; and (d) monitoring at least one of an internal pressure within the first unit operation, an internal pressure within the second unit operation, and an internal pressure within the pressurized vessel, where the first unit operation and the second unit operation include microchannels conveying the first fluid through the first unit operation and conveying the second fluid through the second unit operation.

In a detailed embodiment of the ninth aspect, the first microchannel module includes a plurality of laminated sheets mounted to one another to define internal microchannels of the first unit operation and the second unit operation, where at least one of the internal microchannels of the first unit operation is adjacent to at least one of the internal microchannels of the second unit operation. In a more detailed embodiment, the method includes the step of adjusting the pressure within the pressurized vessel to maintain a predetermined pressure differential between the internal pressure of the pressurized vessel and at least one of the internal pressure of the first unit operation and the internal pressure of the second unit operation. In yet a further detailed embodiment, the method includes the steps of carrying out a fluid medium reaction within the first unit operation, and carrying out a fluid medium reaction within the second unit operation, where thermal energy is exchanged between the first fluid and the second fluid based in part upon the nature of the fluid medium reactions carried out in the first unit operation and the second unit operation.

BRIEF DESCRIPTION OF THE DRAWINGS

FIG. 10 is a schematic representation of fluid flow through an exemplary segment of a microchannel module in accordance with the present invention;

FIG. 11 is a schematic representation of fluid flow through an exemplary repeating unit of a microchannel module in accordance with the present invention;

DETAILED DESCRIPTION

The exemplary embodiments of the present invention are illustrated and described below as steps, procedures, and mechanisms for carrying out desired processes. The various orientational, positional, and reference terms used to describe the elements of the invention are utilized according to such exemplary steps, procedures, and mechanisms. However, for clarity and precision, only a unitary orientational or positional reference will be utilized; and, therefore it will be understood that the positional and orientational references used to describe the elements of the exemplary embodiments of the present invention are only used to describe the elements in relation to one another.

Figure 1:
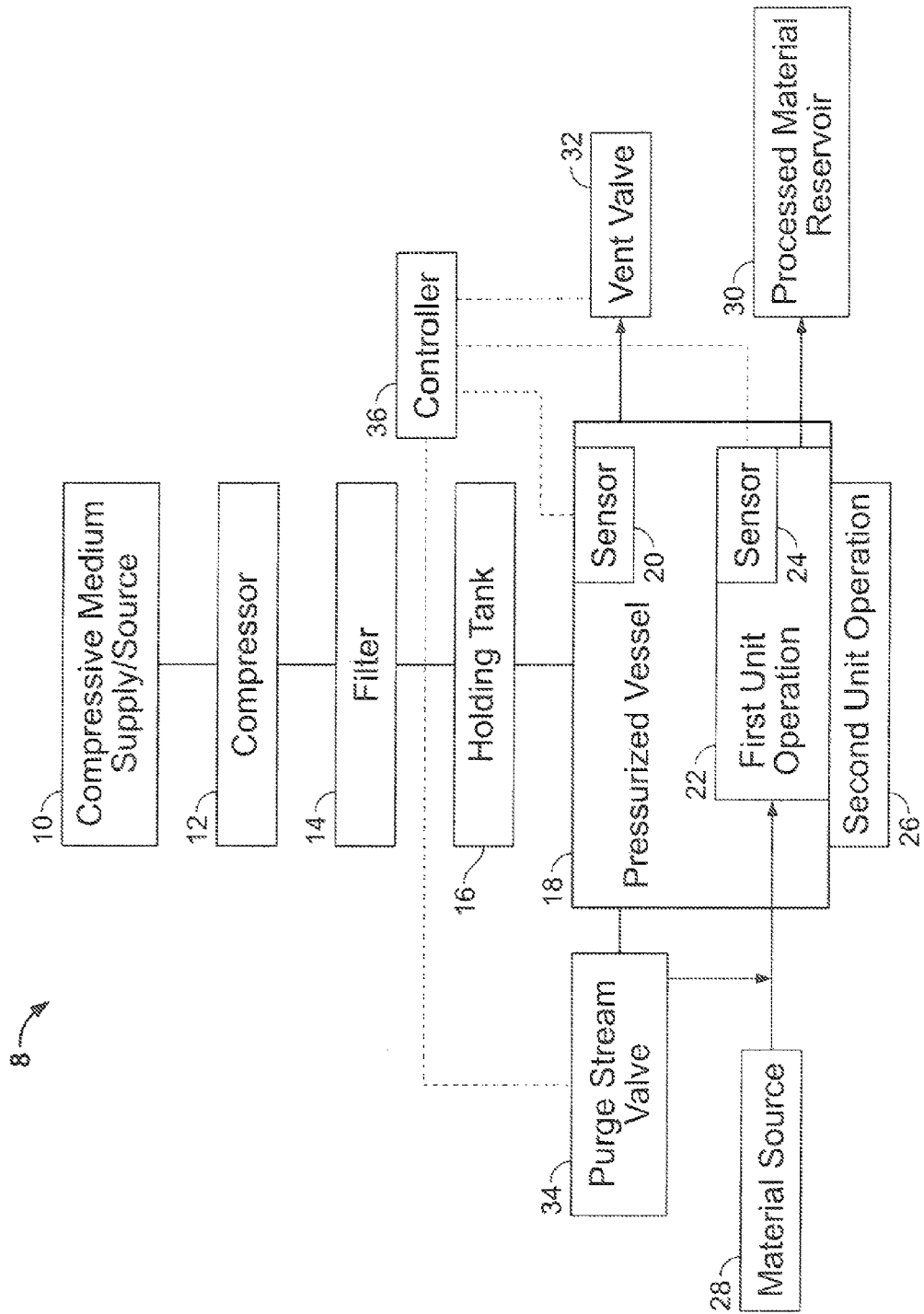
FIG. 1 is a schematic diagram of a first exemplary embodiment of the present invention.

Referring now to the drawings, and in particular to FIG. 1, a first exemplary system 8 includes a compressive medium supply/source 10 in selective fluid communication with an optional compressor/pump 12. The compressive medium contained within the supply/source 10 may be in the form of a gas or a liquid and may likewise include inert fluids known to those of ordinary skill in the art. In a gaseous form, the compressive medium is fed to the compressor 12 prior to filtration of the medium by a filtration unit 14 to remove impurities or particulate matter associated therewith. Those of ordinary skill are familiar with the plethora of filtration operations available and represented by the filtration unit 14. The compressive medium may be deposited within a holding tank 16 in selective fluid communication with a pressurized vessel 18 to provide a filtered and pressurized compressive medium thereto.

The pressurized vessel 18 contains a first unit operation 22 therein that is maintained in compression by the compressive medium occupying interior regions of the pressurized vessel 18 exterior to the first unit operation 22. Both the pressurized vessel 18 and the first unit operation 22 include sensors 20, 24 coupled thereto operative to detect pressures within the pressurized vessel 18 and the first unit operation 22. The first unit operation 22 may include, without limitation, a chemical reactor, a mixer, a chemical separation unit, and a heat exchanger. A chemical separation unit may perform, without limitation, distillation, extraction, absorption, and adsorption. Thus, it is to be understood that a unit operation may perform one or more than one operation.

The first unit operation 22 is adapted to be in fluid communication with a material source 28 and receive material therefrom, while an output conduit carries away processed material from the first unit operation 22 and is adapted to be in fluid communication with a processed material reservoir 30. The first unit operation 22 may include one or more microchannels in exemplary configurations, such as, without limitation, as discussed in U.S. Pat. No. 6,192,596 entitled "Active microchannel fluid processing unit and method of making," and U.S. Pat. No. 6,622,519 entitled "Process for cooling a product in a heat exchanger employing microchannels for the flow of refrigerant and product," each of which is hereby incorporated by reference. Such microchannels may include catalytic agents such as, without limitation, in the form of an interior wall lining, in the form of packed particles, and in the foil of lined or packed inserts adapted to be positioned within the microchannels. The outlet stream of the first unit operation 22 may be in fluid communication and/or thermal communication with one or more additional unit operations, in addition to or in lieu of the process material reservoir. Such an additional unit operation may be adapted to process one or more of the constituents comprising the processed material stream and such an additional unit operation may include, without limitation, a distillation unit separating one or more constituent components thereof.

A second unit operation 26 may be in thermal communication with the first unit operation 22 to allow for thermal energy to be exchanged therebetween. For instance, in an exemplary circumstance where the first unit operation 22 includes a chemical reactor carrying out endothermic reactions, the second unit operation 26 may include a heat exchanger to facilitate providing at least a portion of the thermal energy required to initiate and/or maintain the reactions within the chemical reactor of the first unit operation 22. Such an exemplary second unit operation 26 may be adapted to carry saturated steam into thermal communication with the chemical reactor of the first unit operation 22 and carry away condensed water or lower temperature steam therefrom. Various assemblies and mechanisms capable of facilitating the transfer of thermal energy between unit operations via at least one of convection, conduction, and radiation are well known to those of ordinary skill in the art.

It is likewise within the scope and spirit of the invention for the second unit operation 26 to include a chemical reactor in addition to, or in place of, the heat exchanger. An exemplary chemical reactor of the second unit operation 26 might carry out an exothermic reaction, such as a combustion reaction, providing a thermal energy source available to be transferred to the first unit operation 22 in thermal communication therewith. Likewise, the second unit operation 26 may include a heat exchanger having a high thermal energy fluid flowing therethrough, where a process parameter might require the reduction of the thermal energy content therein that may be achieved by thermal communication between such a fluid and the first unit operation 22. Exemplary processes the first unit operation 22 may carry out where such thermal energy transfer may be advantageous include, without limitation, distillation and endothermic reactions.

It is also within the scope and spirit of the invention for the second unit operation 26 to provide a thermal energy sink in thermal communication with the first unit operation 22. The first unit operation 22, for example, may include a chemical reactor carrying out an exothermic reaction, such as a combustion reaction. Likewise, the first unit operation 22 may include a heat exchanger having a high thermal energy fluid flowing therethrough, where a process parameter might require the reduction of the thermal energy content therein that may be achieved by thermal communication between such a fluid and the second unit operation 26. In such an exemplary circumstance, the second unit operation 26 may include a chemical reactor carrying out an endothermic reaction, a heat exchanger, and/or another process unit adapted to facilitate thermal energy transfer from the first unit operation 22. Those of ordinary skill are familiar with the plethora of such processes falling within such exemplary circumstances.

The pressurized vessel 18 may include a vent valve 32 to vent a portion of the compressive medium contained therein. Exemplary instances where the vent valve 32 may be opened include excess thermal expansion of the compressive medium and shutdown of the first unit operation 22 and/or the second unit operation 26.

The pressurized vessel 18 may further include a purge stream and valve 34 in series therewith to provide selective fluid communication between the compressive medium within the pressurized vessel 18 and the first unit operation 22. In an exemplary configuration, the first unit operation 22 may include a chemical reactor incorporating microchannels and a catalytic agent. In such a configuration, it may be advantageous to provide a generally isothermal stream of compressive medium, optionally an inert medium, during a shutdown procedure of the chemical reactor in order to avoid thermal shock to the first unit operation 22, maintain the integrity of any microchannels therein, and minimize or virtually eliminate thermal fouling of any catalytic agent therein. An exemplary source of generally isothermal compressive medium may include the compressive medium within the pressurized vessel 18. As such, compressive medium from the pressurized vessel 18 may be withdrawn to flow through the purge stream and associated valve 34, into the supply stream, and thereafter into the chemical reactor of the first unit operation 22 to dilute the reactant and reduce the number and/or frequency of reactions occurring therein. Alternatively, or in addition to, the compressive medium of the purge stream may flow directly into the supply stream no longer carrying a significant amount of reactant therein to achieve a complete purge. Likewise, the chemical reactor of the first unit operation 22 may include an inlet within the pressurized vessel 18 where compressive medium may directly and selectively enter therein without utilizing the supply stream. The above exemplary purge processes may also be applicable where process units other than a chemical reactor of the first unit operation 22 are included therewith or in place thereof.

A controller 36 may be operatively coupled to the first sensor 20, the second sensor 24, the vent valve 32, and the valve 34 of the purge stream. The first sensor 20 and the second sensor 24 concurrently detect the respective pressures within the pressurized vessel 18 and the first unit operation 22 and transmit such pressure data to the controller 36. In an exemplary circumstance, it may be advantageous to maintain a higher pressure within the pressurized vessel 18 and a comparatively lower pressure within the first unit operation 22; i.e., a circumstance where the first unit operation 22 is in compression. Upon receiving data from the first sensor 20 and the second sensor 24, a number of actions may be taken by the controller 36 to manipulate such pressures as will be apparent to those of ordinary skill in the relevant art.

It is also within the scope of the present invention to provide more unit operations other than solely the first and second unit operations discussed above. Likewise, it is within the scope of the present invention to provide more than one unit operation within the pressurized vessel, and/or provide more than one unit operation outside of the pressurized vessel that may be in thermal communication therewith. The above discussion is equally applicable to alternate embodiments having more than two unit operations, where more than one unit operation is located within the pressurized vessel or outside thereof. Such alternate embodiments will be obvious to one of ordinary skill after fully appreciating the foregoing.

In an exemplary unit operation startup procedure in accordance with the present invention, the first unit operation 22 may include a chemical reactor in fluid communication with the material source 28. A supply stream coming from the material source 28 may be ramped-up, in concentration and/or in volumetric flow, resulting in more and more material molecules flowing therethrough. Presuming that the chemical reactor of the first unit operation 22 is carrying out a reaction where, on a mole-by-mole basis, a net increase in molecules results from converting reactant (material) to product (processed material), the pressure within the chemical reactor of the first unit operation 22 may increase as more reactant is converted to product, and may also increase from increases in pressure and temperature associated with the inlet stream. The second sensor 24 conveys pressure data to the controller 36 representing any such variance in pressure within the chemical reactor. If the comparative pressure data from the first sensor 20 and second sensor 24 indicate that the pressure within the pressurized vessel 18 is not adequate to maintain the first unit operation 22 in compression within a predetermined tolerance, the controller 36 might direct a valve (not shown) to be opened between the holding tank 16 and the pressurized vessel 18. Compressive medium maintained within the holding tank 16 at a comparatively higher pressure would rush into the pressurized vessel 18 and the resulting increase in pressure would be indicative of pressure data generated by the first sensor 20 and conveyed to the controller 36. The controller 36 would instruct the valve between the pressurized vessel 18 and the holding tank 16 to be closed after the pressure within the pressurized vessel 18 was within a predetermined tolerance of parameters associated with the startup process. This cycle may continue up to, and including, steady state operation if a pressure deficiency is observed by the controller 36.

In an exemplary unit operation shutdown procedure in accordance with the present invention, the first unit operation 22 may include a chemical reactor in fluid communication with the material source 28. The supply stream coming from the material source 28 may be constrained to limit the number of material molecules reaching the first unit operation 22. This constraint may result in the generation of fewer and fewer processed material molecules, presuming the reaction conversion rate remains relatively unchanged. Presuming that the chemical reactor of the first unit operation 22 is carrying out a chemical reaction which, on a mole-by-mole basis, results in a net increase in molecules when reactant (material) is converted to product (processed material), the pressure within the chemical reactor may decrease. Likewise, the pressure and/or temperature of the supply stream may be decreased to decrease the pressure within the chemical reactor of the first unit operation 22. The second sensor 24 conveys pressure data to the controller 36 representative of any variance in pressure within the chemical reactor of the first unit operation 22. If the comparative pressure data from the first sensor 20 and the second sensor 24 indicate that the pressure within the pressurized vessel 18 is higher than a predetermined tolerance, the controller 36 might direct the vent valve 32 to be opened to vent at least a portion of the compressive medium within the pressurized vessel 18, thereby reducing the pressure therein. Compressive medium would exit the higher pressure pressurized vessel 18 until the controller 36 received data from the first sensor 20 indicating that the pressure within the pressurized vessel 18 was within a predetermined tolerance for shutdown and resulting in the vent valve 32 directed closed by the controller 36. Alternatively, in circumstances where the atmospheric pressure is greater than the pressure within the pressurized vessel 18, a compressor or pump (not shown) may be provided in fluid communication therewith to reduce the internal pressure within the pressurized vessel 18.

In the exemplary shutdown procedure discussed above, it may also be advantageous to concurrently purge the chemical reactor of the first unit operation 22 with the compressive medium contained within the pressurized vessel 18. The compressive medium within the pressurized vessel 18 may provide a source of compressive medium that may be relatively isothermal with the chemical reactor of the first unit operation 22 and the contents associated therewith. As the purge valve 34 is directed open by the controller 36 during an exemplary shutdown procedure, compressive medium (optionally inert medium) leaves the higher pressure pressurized vessel 18 and enters the reactant stream, thereafter entering the chemical reactor of the first unit operation 22. As discussed above, the first unit operation 22 may include a direct inlet system (not shown) for allowing compressive medium from the pressurized vessel 18 to flow directly into the first unit operation 22 without use of the supply conduit carrying the reactant stream. The purging of the chemical reactor of the first unit operation 22 with the compressive medium is intended to decrease the number of reactions occurring therein, and in an exothermic reaction cycle, will concurrently act to reduce the temperature of the chemical reactor, presuming that the reactant and/or purge entering the reactor is not at an elevated temperature. As compressive medium leaves the pressurized vessel 18, the first sensor 20 detects the drop in internal pressure and relays this data to the controller 36. The controller 36 may respond to such data by opening the valve between the holding tank 16 and the pressurized vessel 18 to allow more compressive medium to flow into the pressurized vessel, presuming that the pressure differential between the pressurized vessel 18 and the reactor 22 is outside of a predetermined tolerance. The compressive medium flowing into the pressurized vessel 18, from the holding tank 16, may be above, at, or below the temperature of the chemical reactor of the first unit operation 22 and any other contents of the pressurized vessel 18.

One of ordinary skill in the art will readily realize that the present invention does not require the first unit operation 22 to unilaterally withstand high internal pressures exhibited therein. The pressure of the compressive medium, that may optionally include an inert medium, provides a compressive force acting upon the first unit operation 22, thereby providing a counteracting force to any internal pressure developed therein. In sum, components of the first unit operation 22 may be constructed from materials having dimensions not possible but for the pressurized vessel 18 and the counteracting external pressure force acting upon the first unit operation 22.

Figure 2:
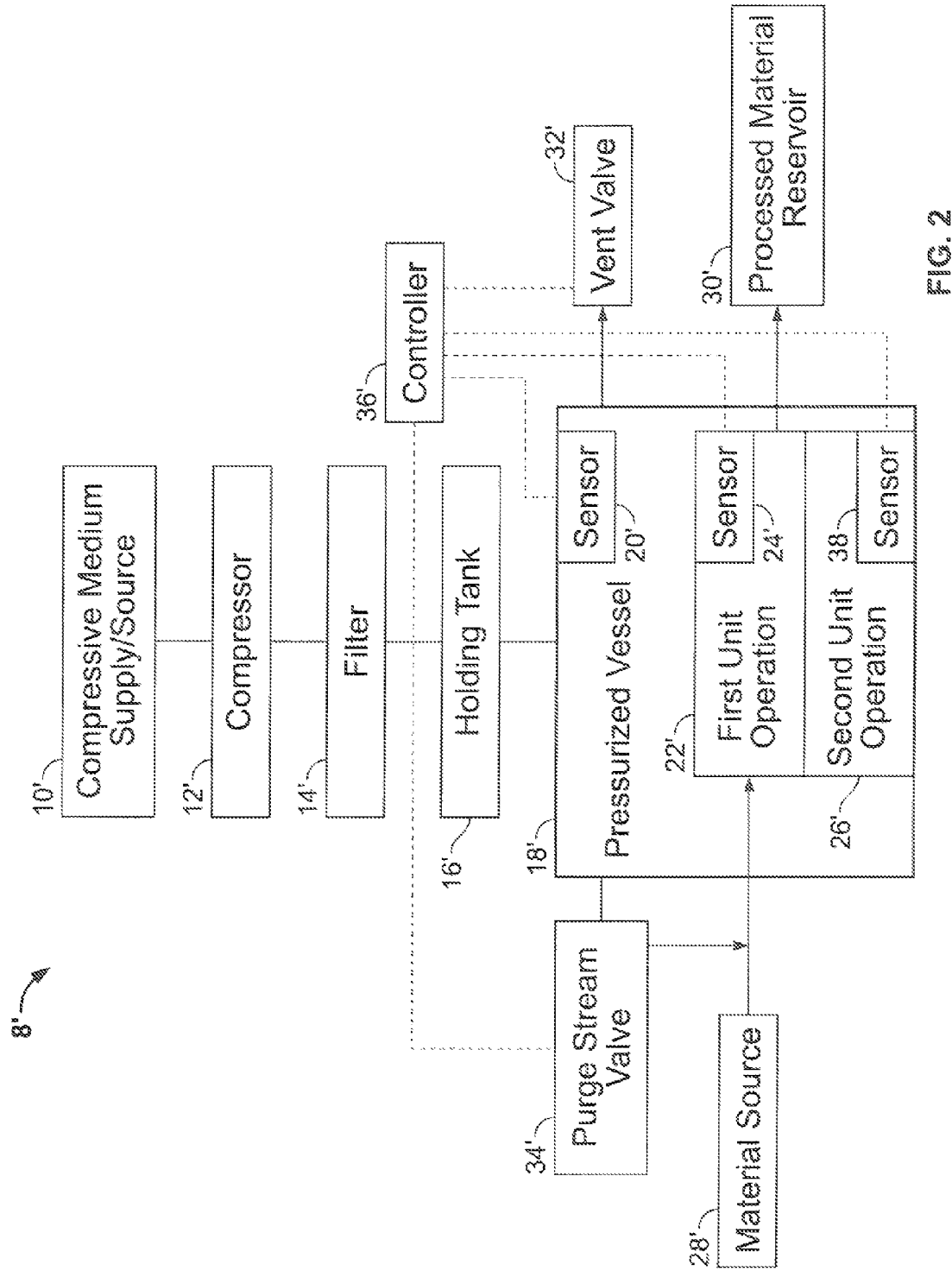
FIG. 2 is a schematic diagram of a second exemplary embodiment of the present invention.

Referring to FIG. 2, a second exemplary system 8' in accordance with the present invention includes a first unit operation 22' and a second unit operation 26' within the pressurized vessel 18'. As discussed above, the first unit operation 22' and the second unit operation 26' may include, without limitation, a chemical reactor, a mixer, a chemical separation unit, and a heat exchanger. Likewise, the first unit operation 22' and the second unit operation 26' may include microchannels and be adapted to be maintained in compression by the compressive medium within the pressurized vessel 18'. Discussion of exemplary processes that may be carried out within the first unit operation 22 of the first exemplary system 8 are equally applicable for the first unit operation 22' and the second unit operation 26' of the second exemplary system 8'. In addition, the second unit operation 26' may include a sensor 38 for detecting pressure within the second unit operation 26' and relaying such information to the controller 36' operatively coupled thereto.

Figure 3:
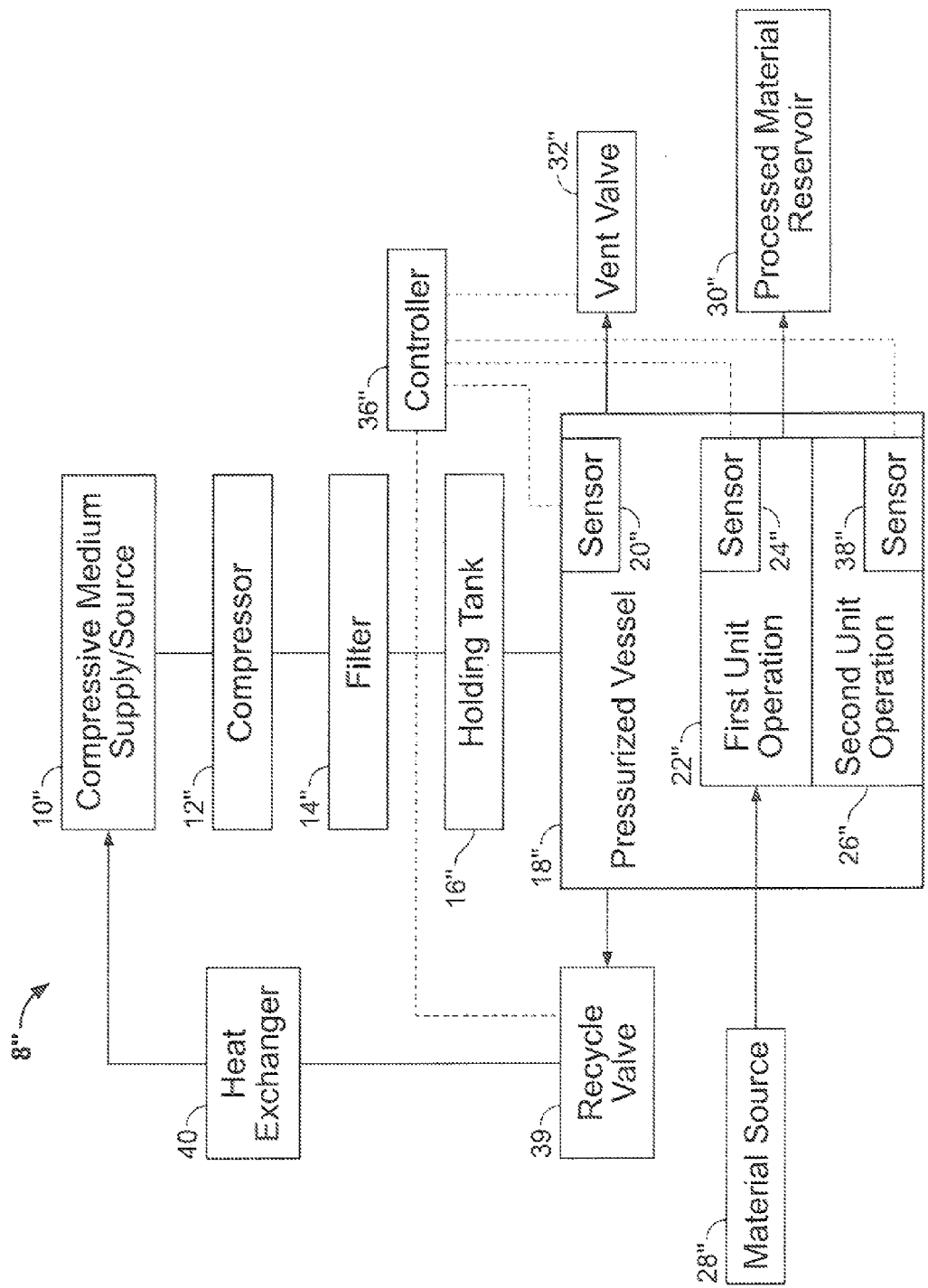
FIG. 3 is a schematic diagram of a third exemplary embodiment of the present invention.

Referencing FIG. 3, a third exemplary system 8" in accordance with the present invention includes a compressive medium supply/source 10" in fluid communication with a compressor 12" outputting the compressed medium to a filtration unit 14". After filtration, the compressed medium may be deposited into a holding tank 16" in fluid communication with a pressurized vessel 18" having a first sensor 20" to monitor the pressure therein. The pressurized vessel 18" contains a first unit operation 22" having a sensor 24" monitoring the pressure therein. A supply stream directs materials from a material source 28" into the first unit operation 22" and an output stream carries processed materials from the first unit operation 22" and to a processed material reservoir 30". The pressurized vessel 18" may also contain a second unit operation 26", with a sensor 38", that may be coupled to and/or in thermal communication with the first unit operation 22". The pressurized vessel 18" may also include a vent valve 32" to selectively vent compressive medium therefrom.

The first unit operation 22" and the second unit operation 26" may include one or more microchannels therein. Such microchannels, as discussed above, may include a catalytic agent in fluid communication with some or all of the supply stream such as in the form of a catalytic lining occupying at least a portion of the internal walls of the microchannels in exemplary configurations where the first unit operation 22" and/or the second unit operation 26" include a chemical reactor.

As discussed previously with respect to the first and second exemplary embodiments 8, 8', the first unit operation 22" and the second unit operation 26" may include, without limitation, a chemical reactor, a mixer, a chemical separation unit, and a heat exchanger. A chemical separation unit may perform, without limitation, distillation, extraction, absorption, and adsorption. As discussed in more detail in the first exemplary embodiment 8, the first unit operation 22" may include a chemical reactor in thermal communication with a chemical reactor of the second unit operation 26". Exemplary shutdown, steady state, and start-up procedures as discussed previously are applicable to the third exemplary embodiment 8", as the pressurized vessel 18" may include a valve (not shown) to provide selective fluid communication between the compressive medium contained therein and the first unit operation 22" and/or the second unit operation 26" to encompass the exemplary purposes discussed above, such as purging, and other purposes apparent to those of ordinary skill. A near isothermal purge fluid, such as the compressive medium within the pressurized vessel 18", may avoid potential equipment damage due to thermally induced stresses otherwise associated with large temperature differences between the purge fluid and the components of the first unit operation 22" and/or the second unit operation 26".

The third exemplary embodiment 8" also includes a recycle stream having a recycle valve 39 in series therewith to provide selective fluid communication between the pressurized vessel 18" and at least one of an auxiliary heat exchanger 40 and the compressive medium source 10". The auxiliary heat exchanger 40 may be utilized to vary the thermal energy associated with the compressive medium cycled therethrough before being directed to the compressive medium supply/source 10".

It is also within the scope and spirit of the present invention to concurrently provide heat transfer from or to the first unit operation 22" and/or the second unit operation 26" via the compressive medium. In such an exemplary procedure it is anticipated that the compressive medium within the pressurized vessel 18" and within the system is sufficient in and of itself to handle the heat loads of the first unit operation 22" without requiring the second unit operation 26" to bear any of the heat load, and vice versa. It is likewise within the spirit of the present invention to enable one unit operation 22", 26" to bear the entire heat load without necessitating the compressive medium within the recycle stream and system to bear a significant duty of the heat load of the alternate unit operation 26", 22". In an exemplary procedure where the first unit operation 22" requires thermal energy added thereto or taken away therefrom, it may be desirable for the second unit operation 26" to be capable of accommodating the entire heat load, and likewise providing the compressive medium and the system associated therewith to be capable of accommodating the entire heat load, such that the complete failure of either the compressive medium and system or a unit operation 26" would allow the other to fully accommodate the thermal energy duty associated with the first unit operation 22", and vice versa.

Figure 4:
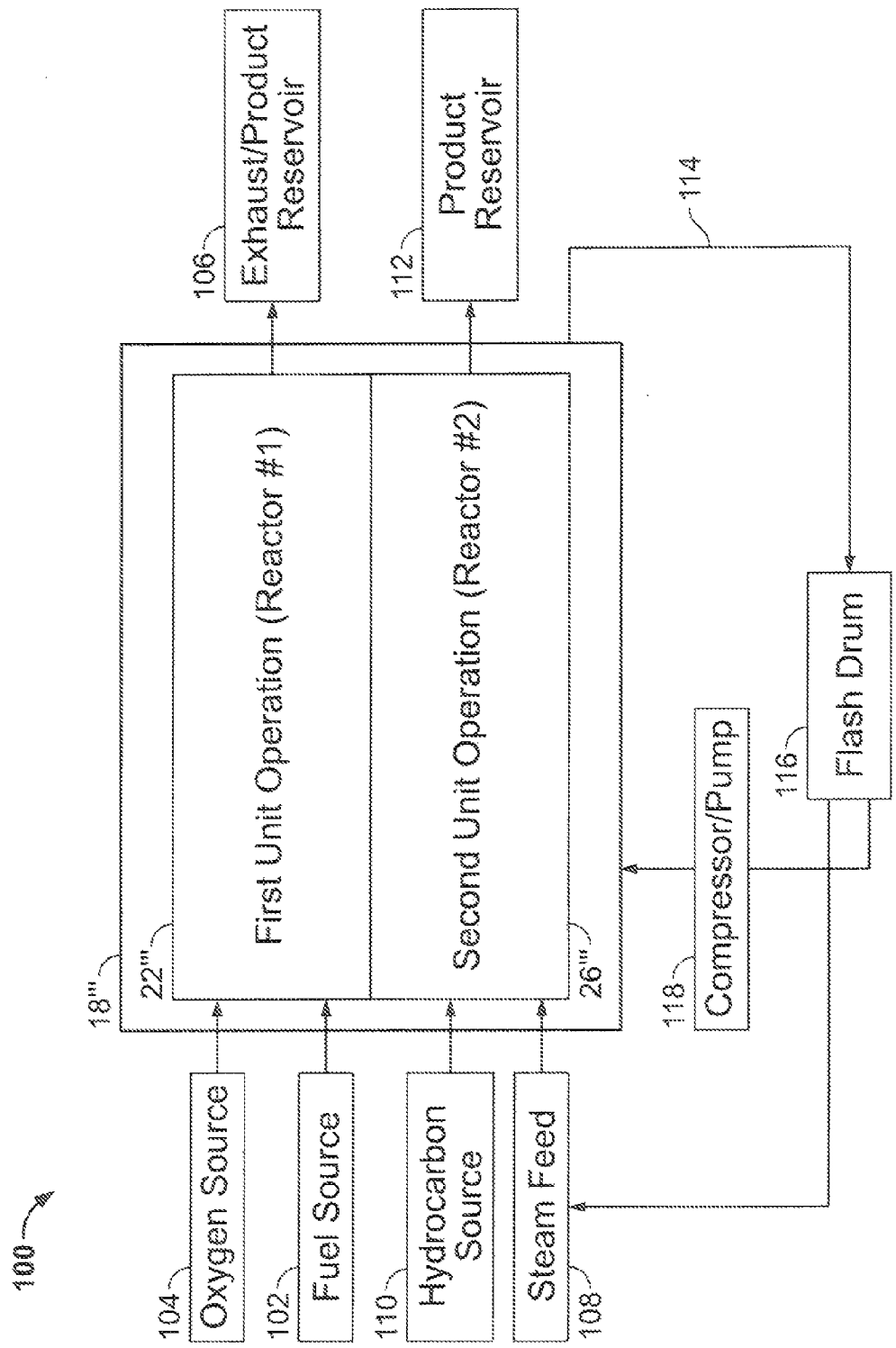
FIG. 4 is a schematic diagram of a first exemplary reaction process carried out in accordance with the present invention.

Referring to FIG. 4, a first exemplary reaction process 100 may be carried out using components described in the first, second, or third exemplary embodiments 8, 8', 8", and obvious variations thereof. However, for purposes of simplicity, not all components analogous to the exemplary components of the first, second, or third exemplary embodiments 8, 8', 8" are shown and/or discussed. A pressurized vessel 18''' contains a compressive medium compressing a first unit operation 22''' adjacent to a second unit operation 26'''. The first unit operation 22''' includes a first chemical reactor carrying out an exothermic reaction process, such as, without limitation, a combustion reaction process. Those of ordinary skill are familiar with such a process and the conditions under which it may be carried out. The second unit operation 26''' includes a second chemical reactor that carries out an endothermic reaction therein, such as, without limitation, steam reformation, in thermal communication with the first chemical reactor.

The first chemical reactor includes microchannels in fluid communication with fuel from a fuel source 102 and oxygen from an oxygen source 104. The microchannels of the first chemical reactor may include catalyst that facilitates the combustion reaction between the fuel and oxygen to result in at least one product and the generation of thermal energy. After combustion, the exhaust/product flows from the first chemical reactor and may be released to the open atmosphere and/or be collected in an exhaust/product reservoir 106.

The second chemical reactor includes microchannels in fluid communication with steam from a steam feed 108 and hydrocarbons from a hydrocarbon source 110. (See U.S. Pat. No. 6,680,044, which is hereby incorporated by reference.) The microchannels of the second chemical reactor may include catalyst that facilitates an endothermic reformation reaction between the steam and hydrocarbons and results in at least one product. After the reaction, the product flows from the second chemical reactor and is directed to a product reservoir 112. It is envisioned that the product reservoir 112 may provide a feed source for one or more downstream unit operations.

The oxygen, fuel, steam and hydrocarbons may travel in a cross current, counter current or co-current direction with respect to the exhaust/product to facilitate thermal energy transfer therebetween. The enhanced heat transfer capabilities offered by microchannels allow thermal energy generated by the combustion reaction to be efficiently transferred to the oxygen, fuel, steam and hydrocarbons flowing therethrough.

The compressive medium within the pressurized vessel 18''' may include high pressure water that is heated by the thermal energy generated from the combustion reaction within the first chemical reactor. A fraction of the high pressure water may be withdrawn from the pressurized vessel 18''' and directed through a recycle conduit 114 where it is flashed into a steam drum 116. The pressure inside the steam drum 116 is considerably less than that within the pressurized vessel 18''' and the recycle conduit 114 which enables a portion of the high temperature high pressure water to change phase and generate saturated steam. The bottoms product, liquid water, is fed to a compressor/pump 118 and cycled back to the pressurized vessel 18''' to absorb thermal energy from the first chemical reactor. The tops product, or steam, is fed to the steam feed 108 that provides steam as a reactant for the steam reformation reaction carried out within the second chemical reactor. Those of ordinary skill are familiar with the various processes that may likewise make use of the steam generated by the first exemplary reaction process 100.

Figure 5:
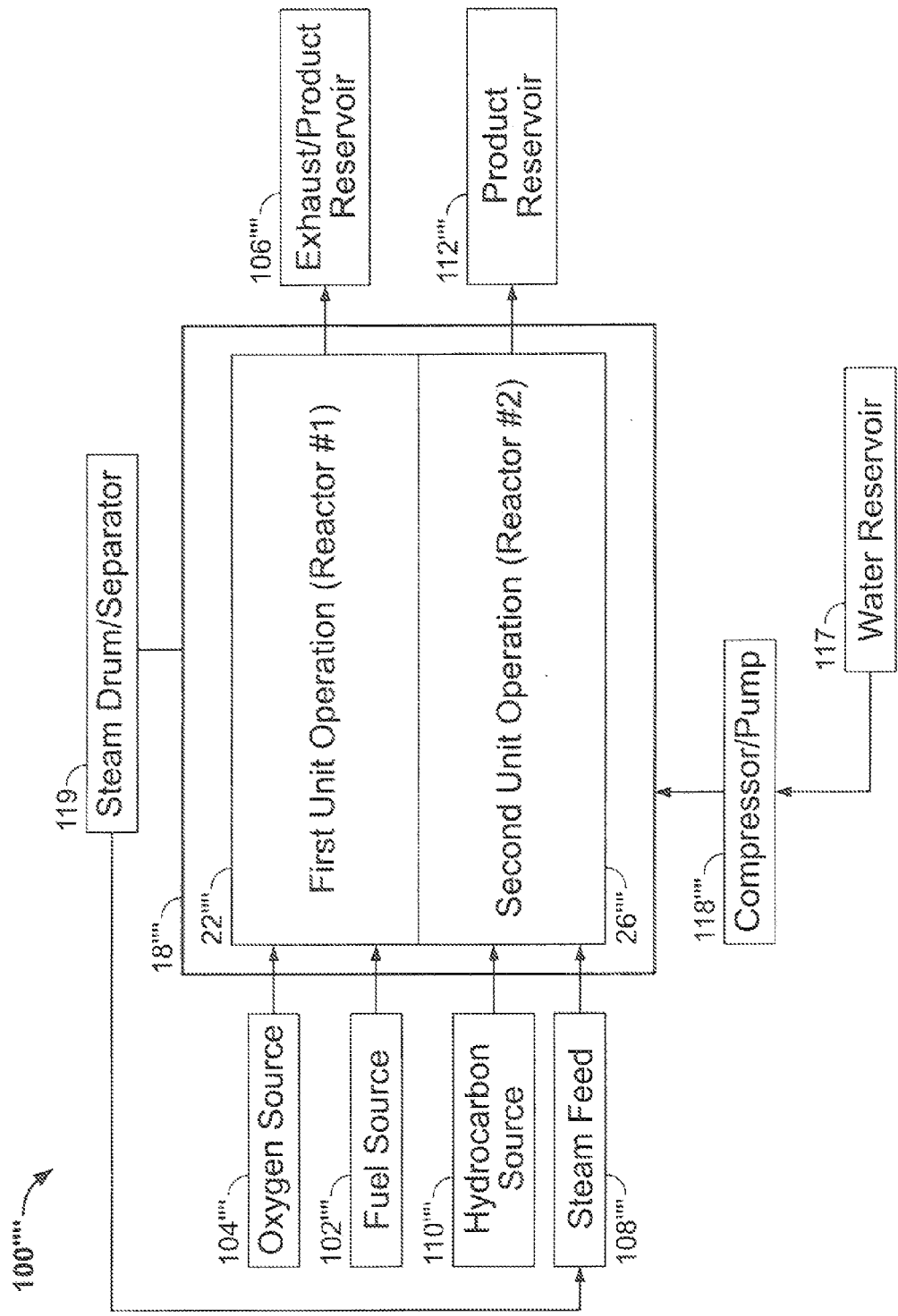
FIG. 5 is a schematic diagram of a first alternate exemplary reaction process carried out in accordance with the present invention.
Figure 6:
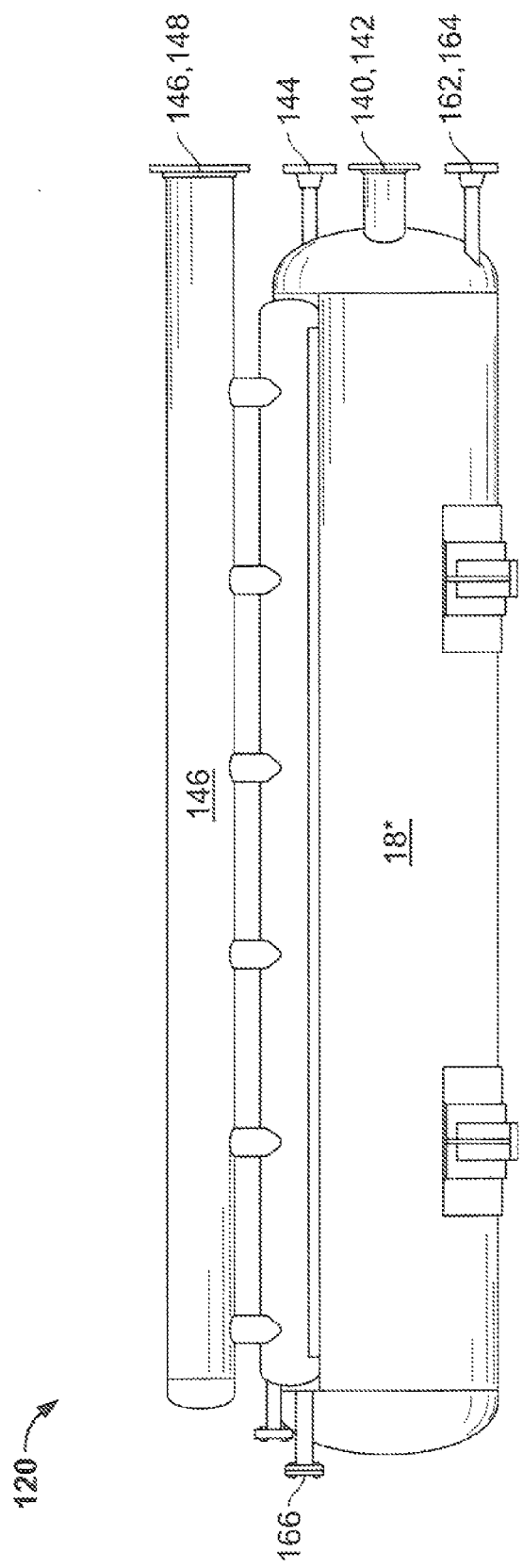
FIG. 6 is a right side view of a first exemplary pressurized vessel in accordance with the present invention.
Figure 7:
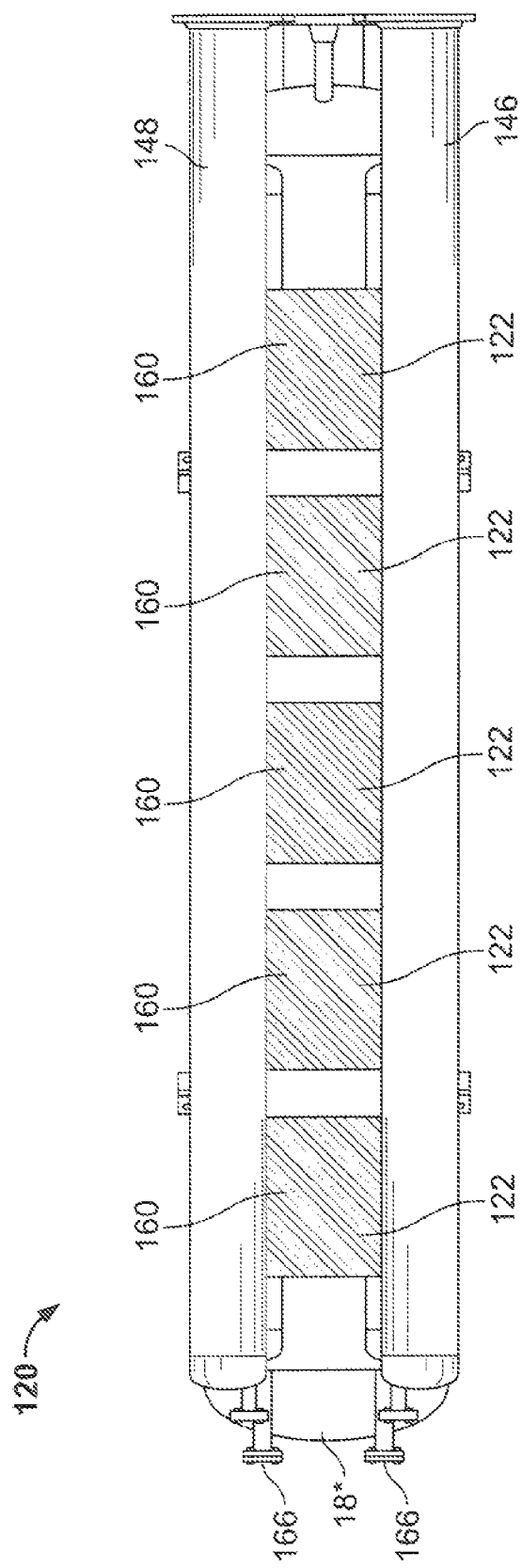
FIG. 7 is an overhead view of the first exemplary pressurized vessel in accordance with the present invention.

Referring to FIG. 5, an alternate first exemplary reaction process 100"" may be carried out using some of the components described in the first reaction process 100, and obvious variations thereof. The reaction process 100"" includes an exothermic reaction within the first unit operation 22"" and an endothermic reaction within the second unit operation 26"". The alternate first exemplary reaction process 100"" includes a water source 117 in fluid communication with the compressor/pump 118"" to provide a source of pressurized water to the pressurized vessel 118"". Those of ordinary skill will understand that a water source is implicit in the first exemplary reaction process 100 discussed previously. Vapor is generated from the water contained in 118"" by the excess heat generated by 22"". A steam drum/separator 119 in fluid communication with the pressurized vessel 118"" contains both water and steam, and provides a source of steam to the steam feed 108"" and second unit operation 26"". The steam and water are separated within the drum 119 prior to the steam being directed to the stream feed 108"".

The reactants and products discussed herein may include fluids, such as, without limitation, gases, liquids, and mixtures thereof that may contain solids. Although the above discussion refers to streams, conduits, and channels, it is to be understood that such process paths may be comprised of a plurality of streams, conduits, and channels. For example, tens, hundreds, thousands, tens of thousands, hundreds of thousands, or millions of separate process paths operating concurrently may be employed with the present invention. For example, a process stream may be comprised of a plurality of individual microchannels that accommodate a requisite volumetric flow, with such microchannels being provided in multiples as needed to accommodate such flow.

Referencing FIGS. 6-9, a first exemplary pressurized vessel unit 120 includes a long cylindrical pressurized vessel 18, 18', 18", 18''', 18"" (collectively 18*) that contains a first unit operation 22, 22', 22", 22''', 22"" (collectively 22*) and a second unit operation 26, 26', 26", 26''', 26"" (collectively 26*) of the exemplary embodiments 8, 8', 8", 8''', 8"" discussed above, where the first unit operation 22* and the second unit operation 26* are combined to form an integrated module 122.

Referencing FIG. 10, an exemplary segment of a module 122 includes a repeating unit 124 that may comprise a series of adjacent microchannels. For purposes of explanation only, the first unit operation 22* and the second unit operation 26* each include a chemical reactor. The first unit operation 22* may include a first microchannel 126 adapted to carry a processed material (product) therein, where the processed material may be the resultant of an endothermic reaction, for example. The first unit operation 22* may also include a second microchannel 128 adapted to carry a material (reactant) therein, isolated adjacently in the repeating unit 124 from, but in fluid communication with, the first microchannel 126. The second unit operation 26* may include a third microchannel 130 that may be adapted to carry a reactant (fuel) therein. The second unit operation 26* may also include a fourth microchannel 132 that may be adapted to carry a reactant (air) therein and be in fluid communication with the third microchannel 130 to selectively mix the reactants in a catalytic portion of the third microchannel 130 where a reaction is carried out to convert the reactants to product. The second unit operation 26* may further include a fifth microchannel 134 that may be adapted to carry a flow of products, isolated adjacently in the repeating unit 124 from, but in fluid communication with, the third and fourth microchannels 130, 132. Whereas, the first and second microchannels 126, 128 are adapted to be separate from, and not in fluid communication with, the third, fourth, and fifth microchannels 130, 132, 134.

Referring to FIG. 11, the repeating unit 124 may be combined with a second repeating unit 124 to create a basic unit 136 that is repeated throughout the module 122. Reference is had to U.S. Pat. No. 6,622,515 entitled "Process for Cooling a Product in a Heat Exchanger Employing Microchannels for the Flow of Refrigerant and Product," U.S. patent application Ser. No. 10/222,196 entitled "Integrated Combustion Reactors and Methods of Conducting Simultaneous Endothermic And Exothermic Reaction," U.S. patent application Ser. No. 10/222,604 entitled "Multi-Stream Microchannel Device," U.S. patent application Ser. No. 10/219,956 entitled "Process for Conducting an Equilibrium Limited Chemical Reaction in a Single Stage Process Channel," and U.S. patent application Ser. No. 10/306,722 entitled "Microchannel Apparatus, Methods of Making Microchannel Apparatus, and Processes of Conducting Unit Operations," for a more detailed explanation of the construction of the module 122, and each disclosure is hereby incorporated by reference.

Referencing FIGS. 6-9, the pressurized vessel unit 120 includes a throughput 140 adapted to receive a supply stream in fluid communication with a material source (not shown), a throughput 142 adapted to receive an output stream in fluid communication with a processed material reservoir (not shown), and a throughput 144 adapted to receive a compressive medium stream in fluid communication with a compressive medium source (not shown). Two headers 146, 148 are mounted to the pressurized vessel unit 120 and include openings 150, 152 therein that are adapted to be in fluid communication with a second material source (not shown), such as a methane holding tank, and third material source (not shown), such as an air tank. The exemplary unit 120 includes five microchannel modules 122 located at least partially therein, with each of the first unit operations 22* in fluid communication with the others 22*, to the exclusion of the second unit operations 26*, and with each of the second unit operations 26* in fluid communication with the others 26*.

Figure 8:
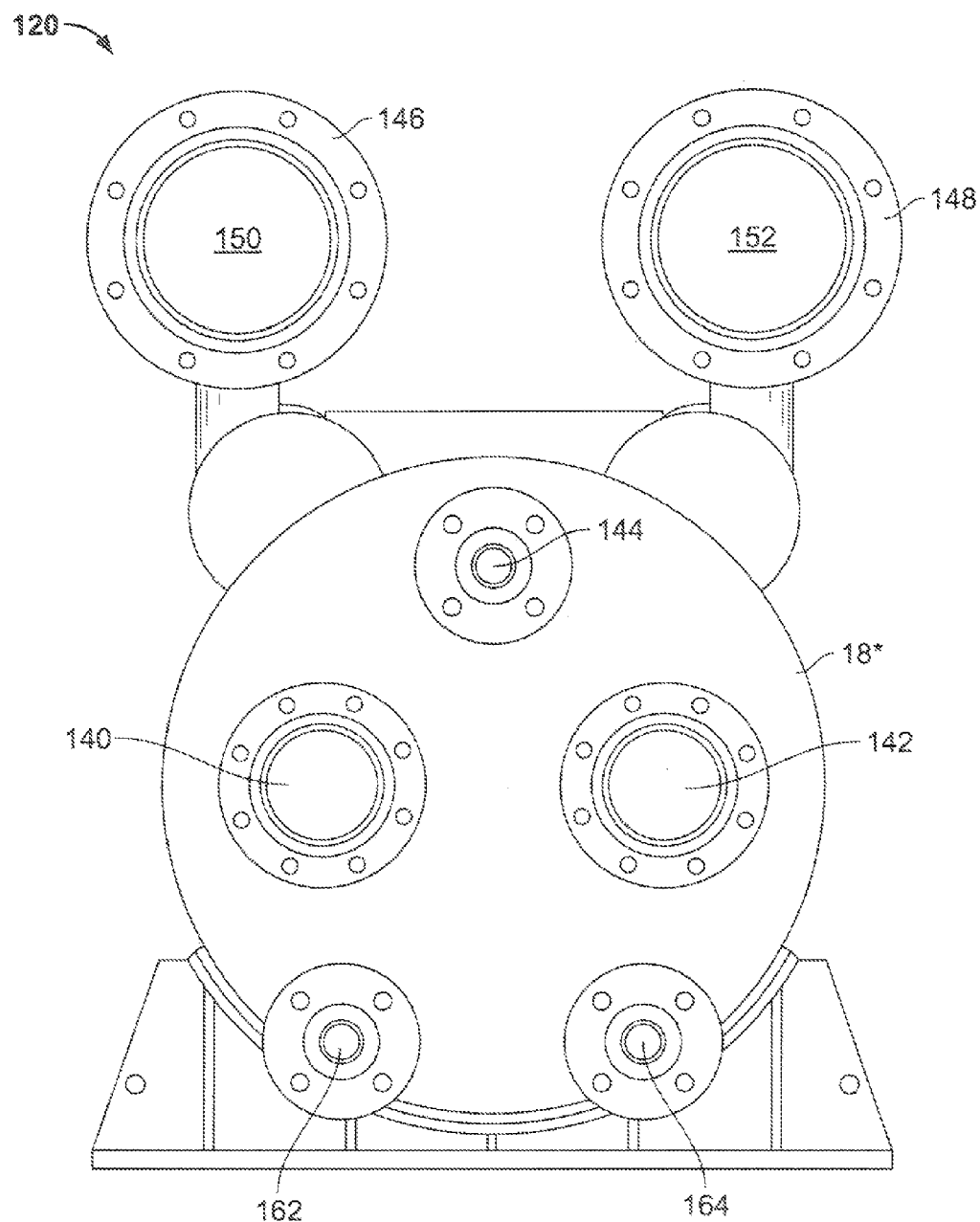
FIG. 8 is an end view of the first exemplary pressurized vessel in accordance with the present invention.
Figure 9:
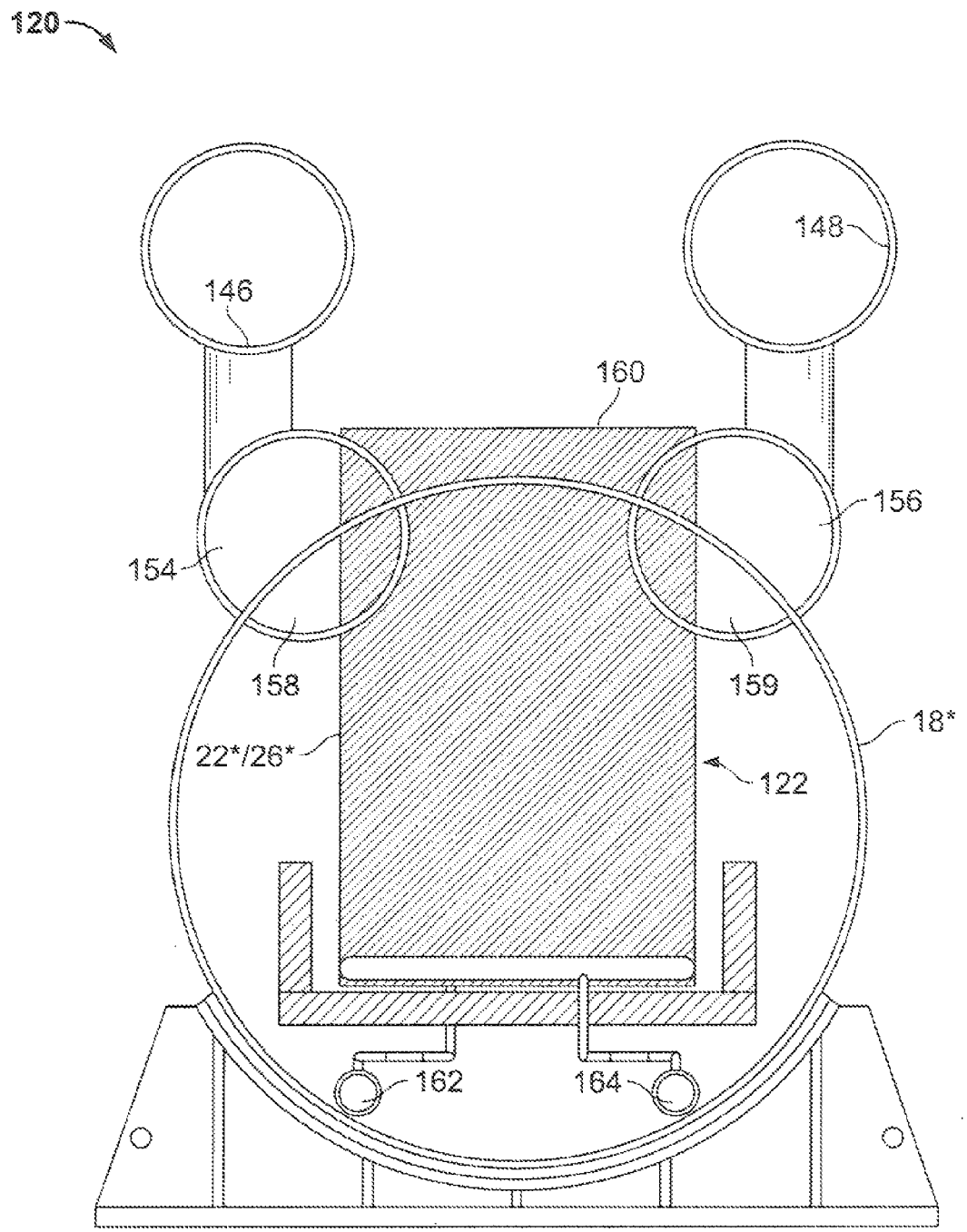
FIG. 9 is a cross-sectional view of the first exemplary pressurized vessel in accordance with the present invention.
Figure 12:
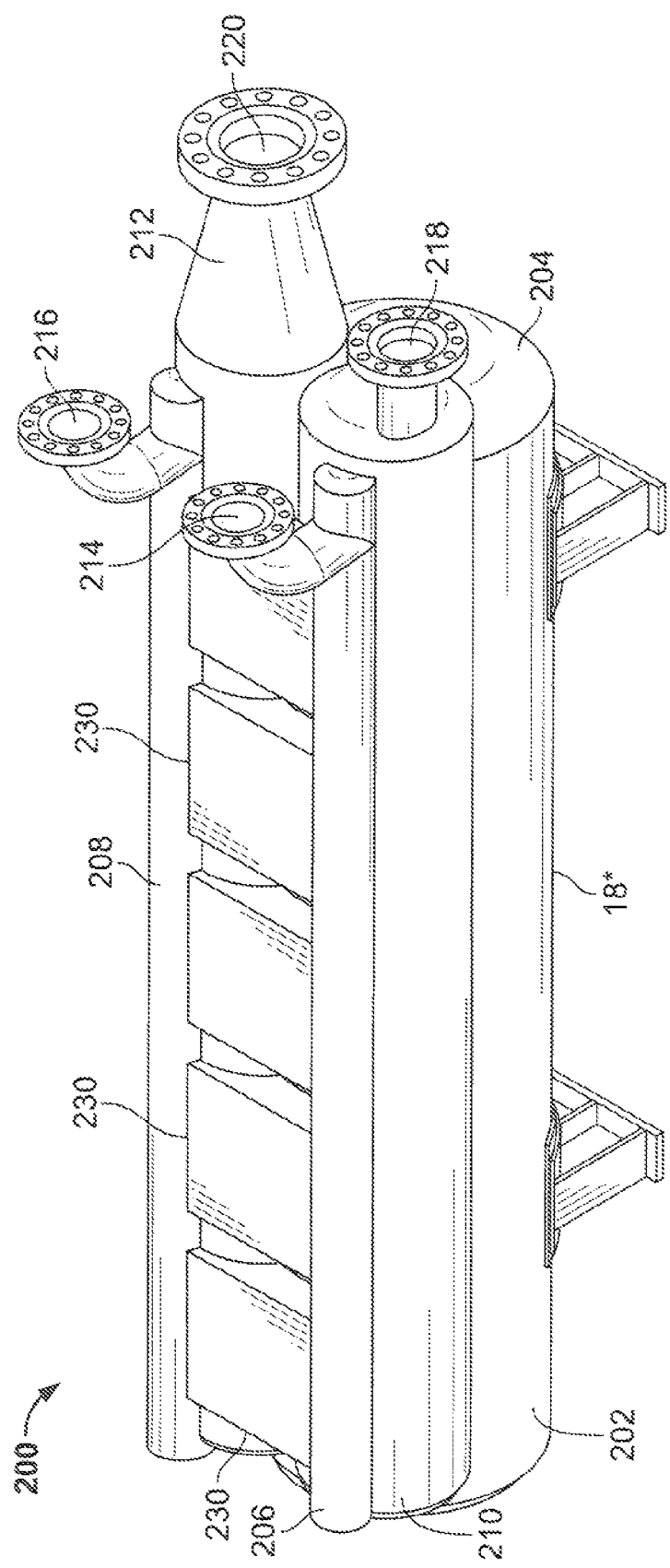
FIG. 12 is an elevated perspective view of a second exemplary pressurized vessel in accordance with the present invention.
Figure 13:
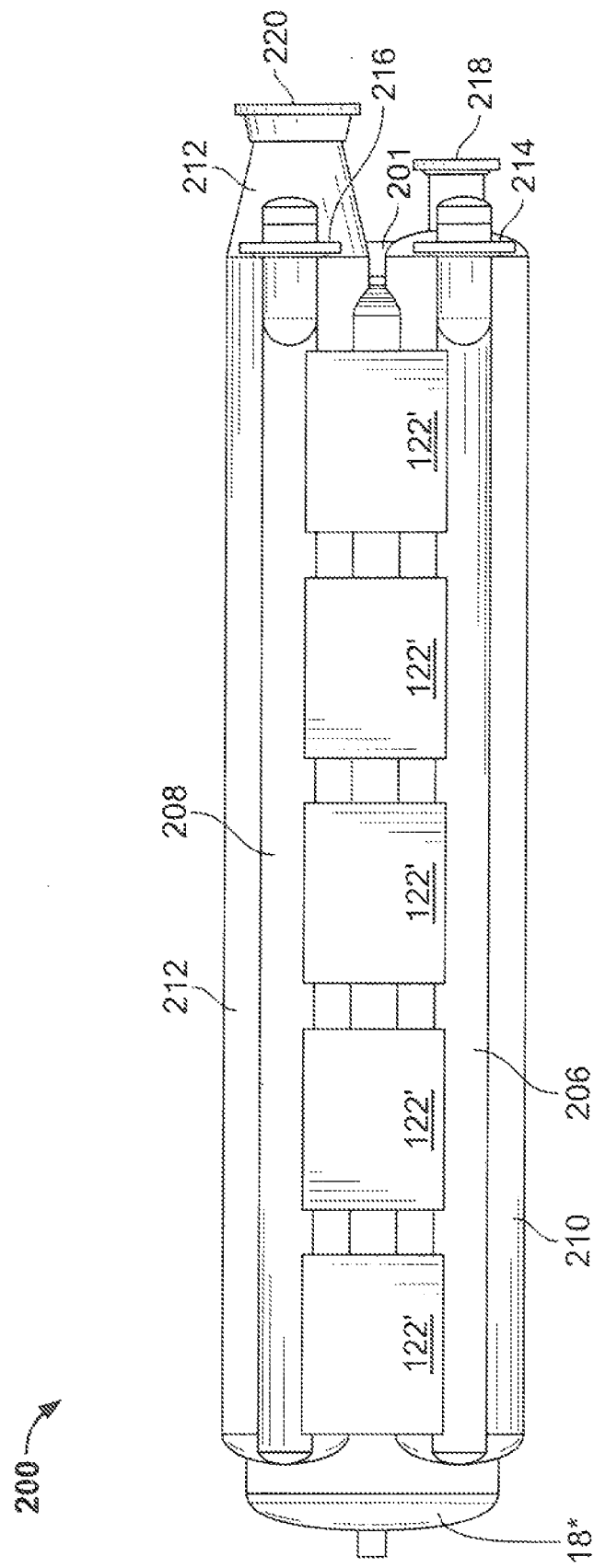
FIG. 13 is an overhead view of the second exemplary pressurized vessel in accordance with the present invention.
Figure 14:
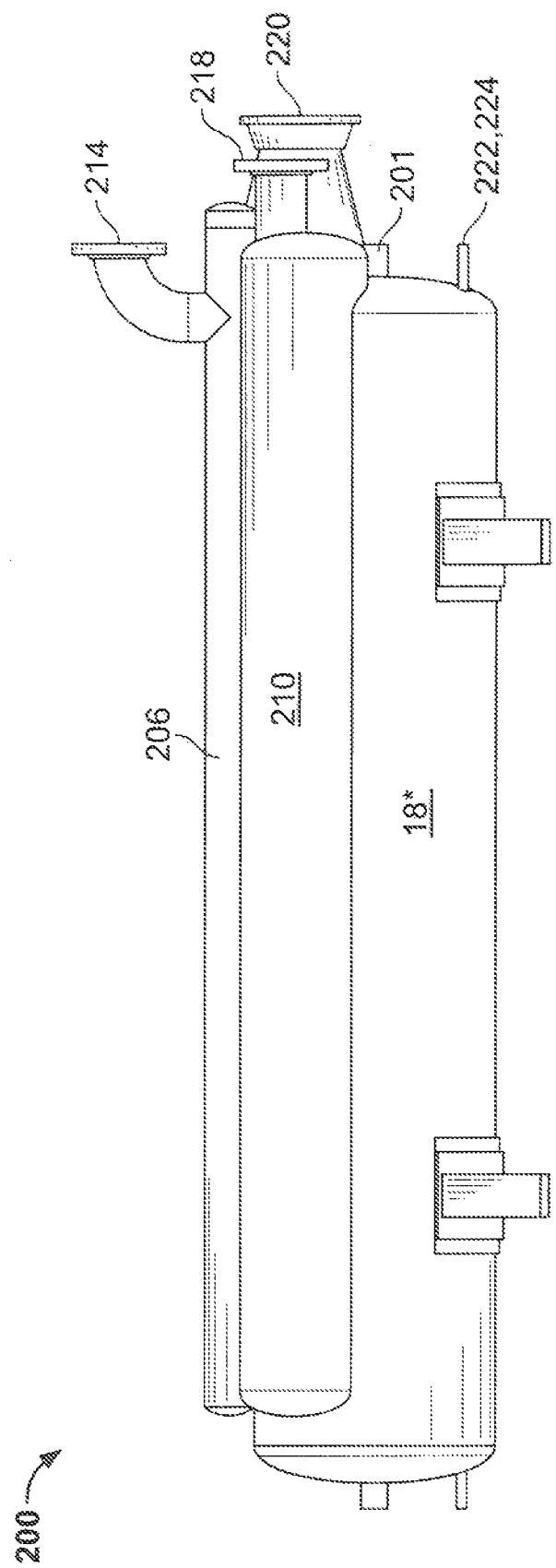
FIG. 14 is a right side view of the second exemplary pressurized vessel in accordance with the present invention.
Figure 15:
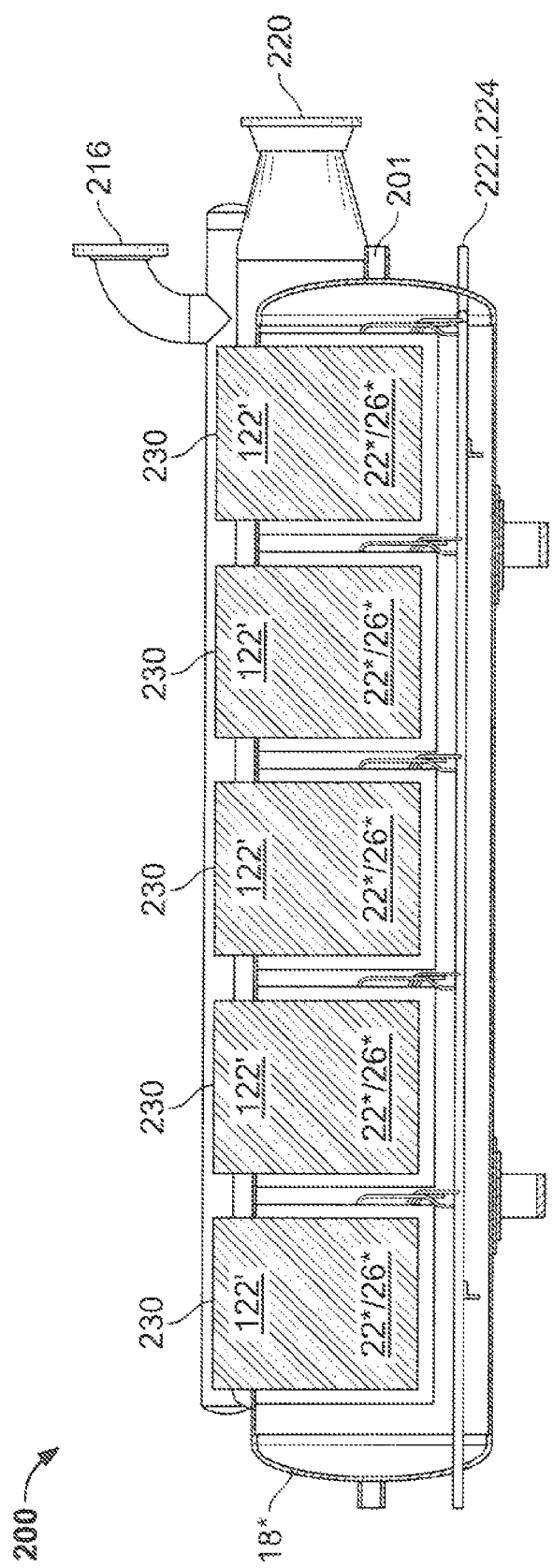
FIG. 15 is a right side cut-away view of the second exemplary pressurized vessel in accordance with the present invention.
Figure 16:
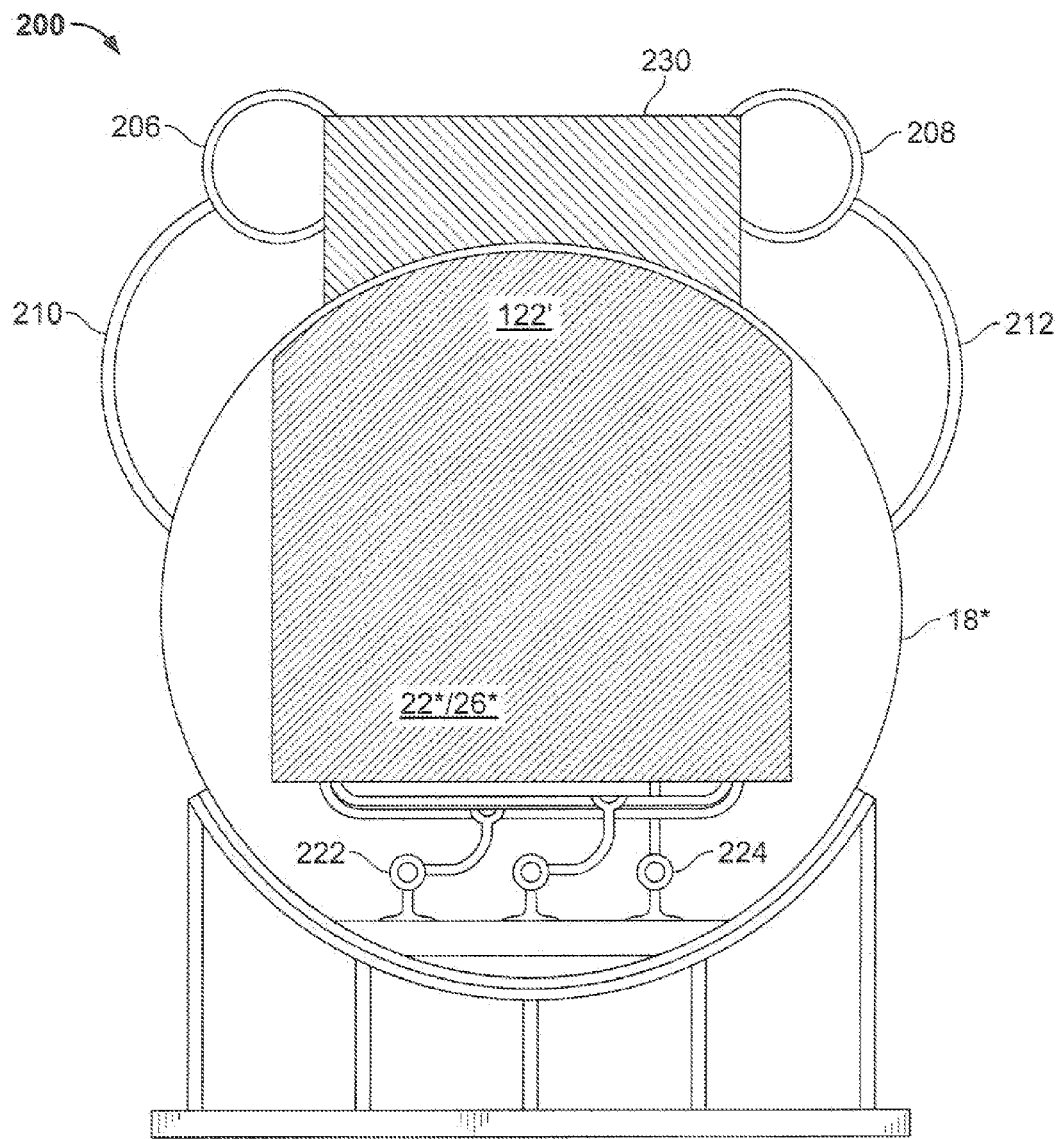
FIG. 16 is a cross-sectional view of the second exemplary pressurized vessel in accordance with the present invention.

Referring to FIGS. 8 and 9, a module 122 is at least partially contained within the pressurized vessel unit 120, such that the first unit operation 22* and the second unit operation 26* are adapted to be in compression. A conduit 154 in fluid communication with the header 146 may provide a supply stream to the second unit operation 26*, while a conduit 156 in fluid communication with the header 148 may likewise carry a supply stream to the second unit operation 26*. An internal conduit 158 in fluid communication with the throughput 140 (See FIG. 8) may provide a material, such as a reactant, to the first unit operation 22*, while an internal conduit 159 in fluid communication with a throughput 142 (See FIG. 8) may carry away processed material, such as a product, from the first unit operation 22*. In an exemplary combustion reaction occurring within the second unit operation 26*, the conduit 154 may carry a hydrocarbon and the other conduit 156 may carry oxygen, air, or another oxygen source. The exhaust or product stream from the second unit operation 26* may be vented through a port 160 approximate the exposed portion of the module 122. It is also within the scope and spirit of the present invention to capture the exhaust/product by placing a manifold over the port 160 and directing the exhaust/product to a subsequent process unit (not shown).

The pressurized vessel unit 120 may also include two or more refurbishment lines 162, 164 for catalyst regeneration within the unit operations 22*, 26*. Optionally, the pressurized vessel unit 120 may include flanged conduits 166 to be utilized as inspection ports for the unit operations 22*, 26* contained therein. Such flanged conduits 166 would typically be flanged closed under normal operation of the pressurized vessel unit 120 and unit operations 22*, 26* contained therein.

Referencing FIGS. 11-15, a second exemplary pressurized vessel unit 200 includes a long cylindrical pressurized vessel 18* that houses the first unit operation 22* and the second unit operation 26* therein under a compressive force supplied by a compressive medium also housed therein and entering via an opening 201. As discussed with respect to the first exemplary pressurized vessel unit 120, the first unit operation 22*, and the second unit operation 26* may each include a microchannel chemical reactor for purposes of explanation only.

The unit 200 is sealed at both longitudinal ends 202, 204 with respect to an external environment and may include five microchannel modules 122', at least partially housed therein, in selective fluid communication with headers 206, 208, 210, 212 mounted exteriorly thereto. A first header 206 includes a supply stream inlet 214 in fluid communication with a reactor of the first unit operation 22*, while a second header 208 includes an output stream outlet 216 also in fluid communication with the first unit operation 22*. A third header 210 includes a supply stream inlet 218 in fluid communication with a reactor of the second unit operation 26*, and a fourth header 212 includes a supply stream inlet 220 in fluid communication with the second unit operation 26*. As discussed above, each module 122' may comprise a first unit operation and a second unit operation including microchannels therein, and thus, the headers 206, 208, 210, 212 provide fluid communication with the respective modules 122.

In an exemplary steam reformation reaction carried out within the first unit operation 22*, the first header 206 may carry steam and methane (material) and the second header 208 may carry hydrogen, carbon dioxide, and carbon monoxide (processed material). In an exemplary combustion reaction within the second unit operation 26*, the third header 208 may carry a hydrocarbon (reactant or fuel) and the fourth header 210 may carry air or another oxygen source (reactant). The exhaust or product stream from the second unit operation 26* may be vented through a port 230 approximate the exposed portion of the module 122'. It is also within the scope of the present invention to capture the exhaust/product by placing a manifold over the port 230 and direct the exhaust/product to a subsequent process unit (not shown).

The pressurized vessel unit 200 may also include two or more refurbishment lines 222, 224 (not shown in FIGS. 12 and 13) for catalyst regeneration within the reactors of the unit operations 22*, 26*. Optionally, the pressurized vessel unit 200 may include flanged conduits (not shown) to be utilized as inspection ports for the unit operations 22*, 26*. Such flanged conduits would typically be flanged closed under normal operation of the pressurized vessel unit 200.

As will be understood by one skilled in the art, the exemplary pressurized vessel units 120, 200 shown in FIGS. 6-9 and 12-16 are wholly exemplary in nature and may be further configured to include features discussed in any of the exemplary embodiments above.

The present invention has been described above with respect to exothermic and endothermic reactions in general, and combustion and reformation reactions as more specific examples, however, the present invention is applicable for carrying out other reactions, such as, without limitation, acetylation, addition reactions, alkylation, dealkylation, hydrodealkylation, reductive alkylation, amination, ammoxidation aromatization, arylation, autothermal reforming, carbonylation, decarbonylation, reductive carbonylation, carboxylation, reductive carboxylation, reductive coupling, condensation, cracking, hydrocracking, cyclization, cyclooligomerization, dehalogenation, dehydrogenation, oxydehydrogenation, dimerization, epoxidation, esterification, exchange, Fischer-Tropsch, halogenation, hydrohalogenation, homologation, hydration, dehydration, hydrogenation, dehydrogenation, hydrocarboxylation, hydroformylation, hydrogenolysis, hydrometallation, hydrosilation, hydrolysis, hydrotreating (including hydrodesulferization HDS/HDN), isomerization, methylation, demethylation, metathesis, nitration, oxidation, partial oxidation, polymerization, reduction, reformation, reverse water gas shift, Sabatier, sulfonation, telomerization, transesterification, trimerization, and water gas shift.

For each of the exemplary reactions listed above, there are catalysts and conditions known to those skilled in the art for carrying out such reactions that likewise fall within the scope and spirit of the present invention. For example, the invention contemplates methods of amination through an amination catalyst and apparatuses containing the amination catalyst. In sum, the invention can be described for each of the reactions listed above, either individually (e.g., hydrogenolysis), or in groups (e.g., hydrohalogenation, hydrometallation and hydrosilation with hydrohalogenation, hydrometallation and hydrosilation catalyst, respectively).

Following from the above description and invention summaries, it should be apparent to those of ordinary skill in the art that, while the apparatuses and methods described herein and illustrated constitute exemplary embodiments of the present invention, it is understood that the invention is not limited to these precise embodiments and that changes may be made therein without departing from the scope of the invention as defined by the claims. Additionally, it is to be understood that the invention is defined by the claims and it is not intended that any limitations or elements describing the exemplary embodiments set forth herein are to be incorporated into the claims unless explicitly recited in the claims themselves. Likewise, it is to be understood that it is not necessary to meet any or all of the recited advantages or objects of the invention disclosed herein in order to fall within the scope of any claim, since the invention is defined by the claims and since inherent and/or unforeseen advantages of the present invention may exist even though they may not have been explicitly discussed herein.

What is claimed is:

1. A method of starting up one or more units, the method comprising the steps of:
   starting up a first unit including microchannels therein by initially feeding a material to the first unit and through the microchannels;
   processing, within the first unit, at least a portion of the material;
   monitoring at least one of internal pressure, temperature, and concentration at least one of within the first unit or downstream from the first unit;
   partially containing the first reactor using a containment device so that at least a portion of the reactor is not contained by the containment device; and
   pressurizing the containment device with a compressive medium to maintain a pressure differential between an internal pressure within the containment device and an internal pressure within the first unit such that the internal pressure within the containment device is greater than the internal pressure within the first unit.

2. The method of claim 1, further comprising the step of adjusting the internal pressure within the containment device to track the internal pressure within the first unit.

3. The method of claim 1, wherein the first unit includes a tubular flow reactor.

4. The method of claim 1, wherein the pressurizing step includes the step of monitoring the internal pressure within the containment device.

5. The method of claim 1, wherein the pressurizing step includes providing selective fluid communication between the containment device and a compressive medium source.

6. The method of claim 1, wherein the compressive medium includes at least one of an inert medium, the material fed to the first unit, and the processed material exiting the first unit.

7. The method of claim 1, further comprising the steps of:
   feeding a composition to a second unit;
   processing, within the second unit, at least a portion of the composition;
   monitoring at least one of internal pressure, temperature, and concentration at least one of within the second unit or downstream from the second unit; and
   pressurizing the containment device, at least partially containing the second unit therein, with the compressive medium to maintain the pressure differential between the internal pressure within the containment device and an internal pressure within the second unit such that the internal pressure within the containment device is greater than the internal pressure within the second unit.

8. The method of claim 7, wherein the second unit includes microchannels through which the composition may flow therethrough.

9. The method of claim 1, wherein:
   the material comprises steam and methane;
   the microchannels of the first unit comprise a microchannel reactor; and processing of the material includes reacting the steam and the methane as part of a steam reformation reaction.

10. The method of claim 9, wherein:
the compressive medium includes water; and
at least a portion of the water comprises steam that is conveyed to the microchannel reactor.

11. The method of claim 9, wherein the containment device is pressurized prior to feeding the material to the microchannel reactor.

12. The method of claim 1, wherein:
the material comprises hydrogen and carbon monoxide;
the microchannels of the first unit comprise a microchannel reactor; and
processing of the material includes reacting the hydrogen and carbon monoxide as part of a Fischer-Tropsch reaction.

13. The method of claim 12, wherein monitoring step includes monitoring a concentration of hydrocarbon product resulting from the Fischer-Tropsch reaction downstream from the microchannel reactor.

14. The method of claim 12, wherein:
the compressive medium includes water; and
at least a portion of the water comprises steam that is conveyed outside the containment device.

15. The method of claim 12, wherein the containment device is pressurized prior to feeding the material to the microchannel reactor.

16. A method of starting up one or more units, the method comprising the steps of:
starting up a first unit including microchannels therein by initially feeding a material to the first unit and through the microchannels;
processing, within the first unit, at least a portion of the material;
monitoring at least one of internal pressure, temperature, and concentration at least one of within the first unit or downstream from the first unit; and
pressurizing a containment device, partially containing the first unit therein, with a compressive medium to maintain a pressure differential between an internal pressure within the containment device and an internal pressure within the first unit such that the internal pressure within the containment device is greater than the internal pressure within the first unit;
wherein the compressive medium includes water; and,
wherein at least a portion of the water comprises steam that is conveyed to the microchannel reactor.

* * * * *